United States Patent
Li

(10) Patent No.: US 8,697,857 B2
(45) Date of Patent: Apr. 15, 2014

(54) SOYBEAN EF1A2 PROMOTER AND ITS USE IN CONSTITUTIVE EXPRESSION OF TRANSGENIC GENES IN PLANTS

(75) Inventor: Zhongsen Li, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 783 days.

(21) Appl. No.: 12/274,443

(22) Filed: Nov. 20, 2008

(65) Prior Publication Data

US 2009/0133159 A1    May 21, 2009

Related U.S. Application Data

(60) Provisional application No. 60/989,172, filed on Nov. 20, 2007.

(51) Int. Cl.
  *C12N 15/82*  (2006.01)
  *C12N 15/87*  (2006.01)
  *C12N 15/63*  (2006.01)

(52) U.S. Cl.
  USPC ........ 536/24.1; 435/320.1; 800/287; 800/278

(58) Field of Classification Search
  USPC ...................................... 536/24.1
  See application file for complete search history.

(56) References Cited

U.S. PATENT DOCUMENTS

2002/0042931 A1 *   4/2002   Kaplan et al. ................. 800/290

OTHER PUBLICATIONS

Shoemaker et al. 2006, Genbank Accession No. ED622561.*
Aguilar et al. Plant Molecular Biology, vol. 17(3), p. 351-360, 1991.
Axelos et al. Molecular Gen. Genetics, vol. 219, p. 106-112, 1989.
Aida et al. Japan Agriculture Research Quarterly, vol. 39(4), p. 269-274, 2005.
Nakane et al. Journal Gen. Plant Pathol., vol. 69, p. 378-384, 2003.
Shewmaker et al. Nucleic Acids Res., vol. 18(14), p. 4276, 1990.
Wang et al. Journal Biol. Chem, vol. 274(17), p. 12001-12008, 1999.
Kawahara et al. Eur. J. Biochem, vol. 209(1), p. 157-162, 1992.

* cited by examiner

*Primary Examiner* — Li Zheng

(57) ABSTRACT

The promoter of a soybean translation elongation factor EF1 alpha, a polypeptide that promotes the GTP-dependent binding of aminoacyl-tRNA to the A-site of ribosomes during protein biosynthesis, and fragments thereof and their use in promoting the expression of one or more heterologous nucleic acid fragments in a tissue-independent or constitutive manner in plants are described.

18 Claims, 11 Drawing Sheets

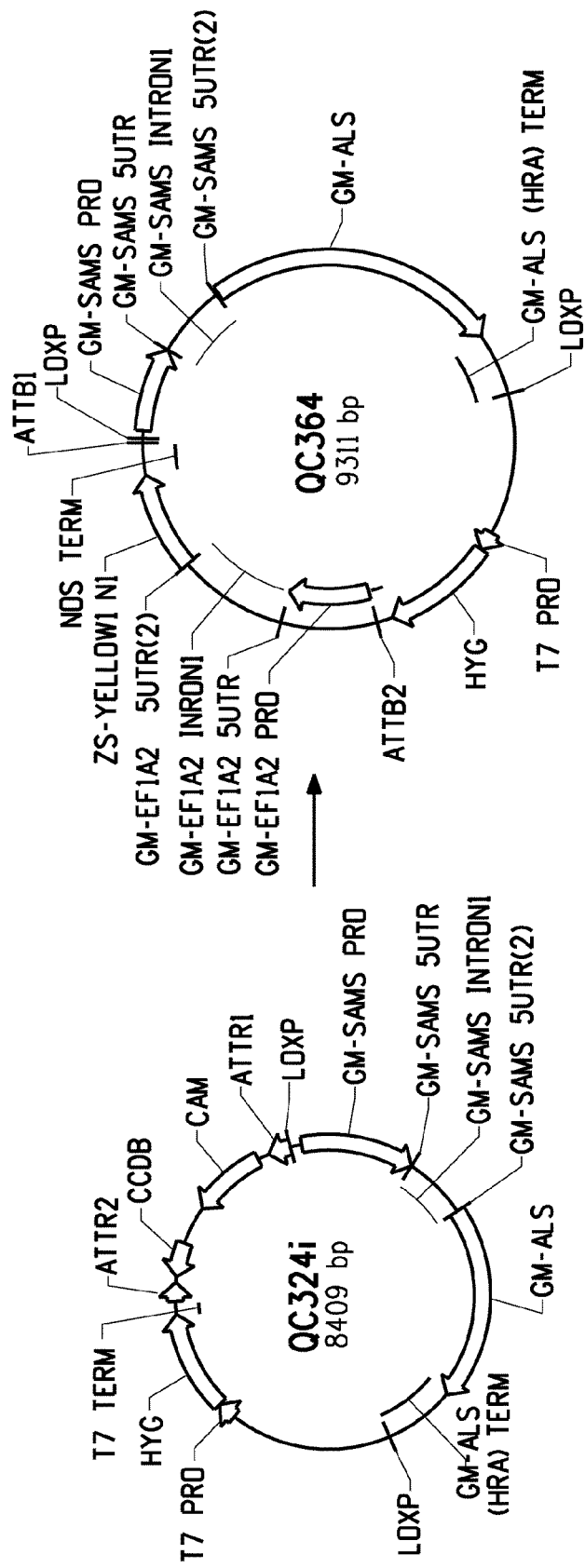

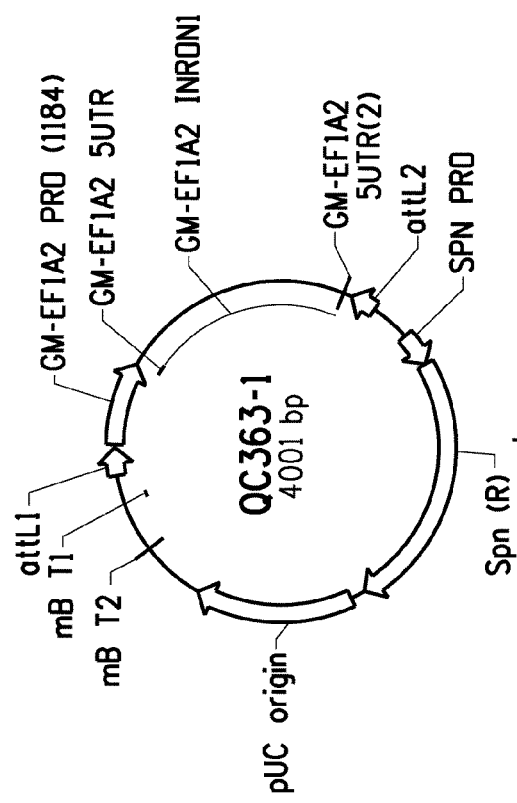
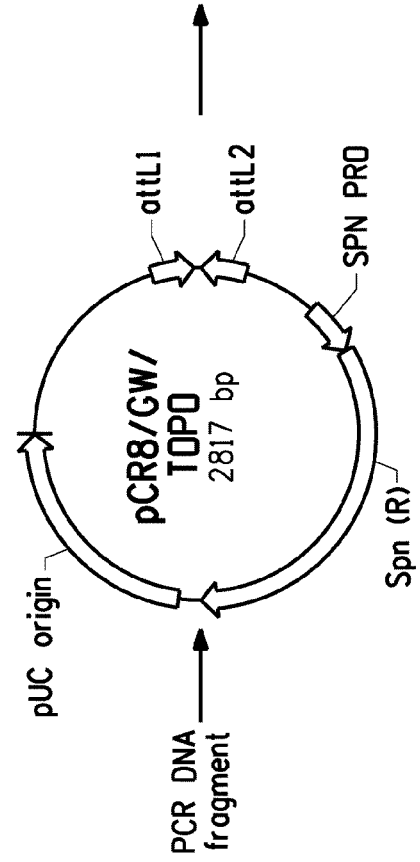
FIG. 4B
FIG. 4A

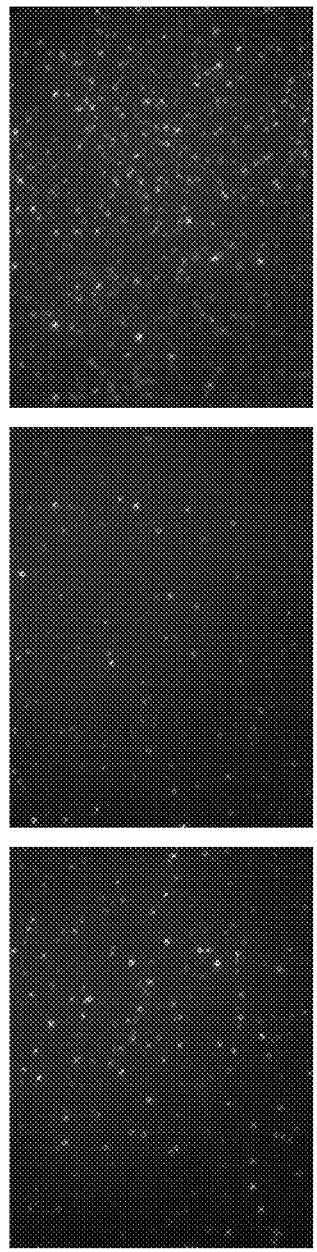
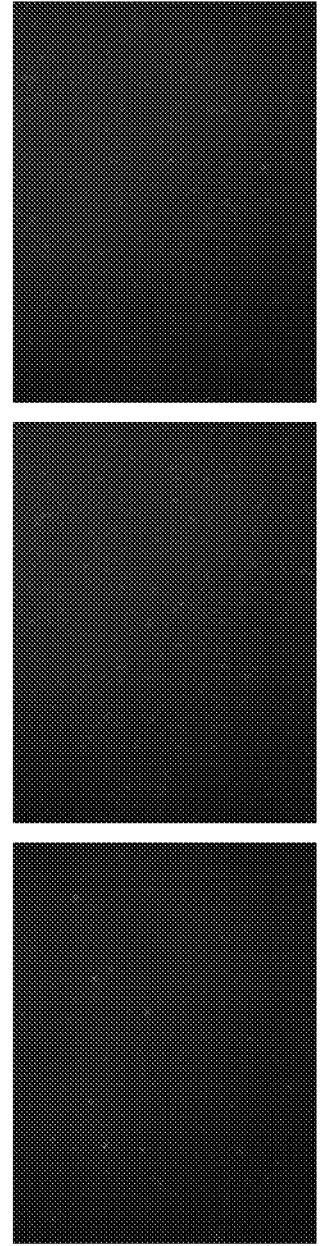
FIG. 6A QC363
FIG. 6B QC363-1Y
FIG. 6C QC363-2Y
FIG. 6D QC363-3Y
FIG. 6E QC363-4Y
FIG. 6F QC363-5Y

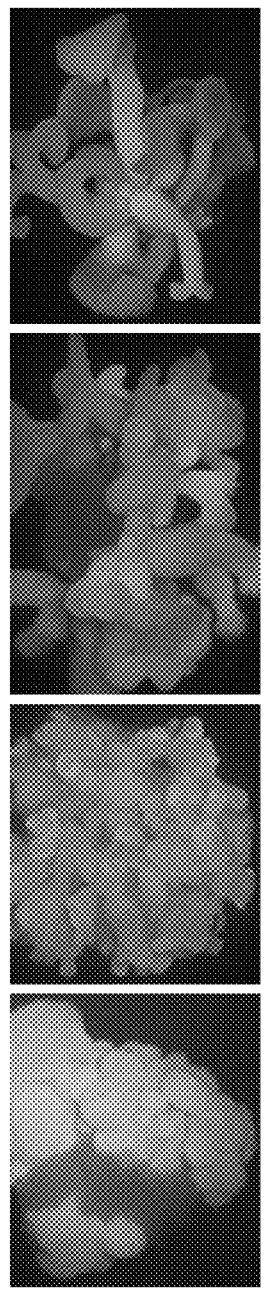
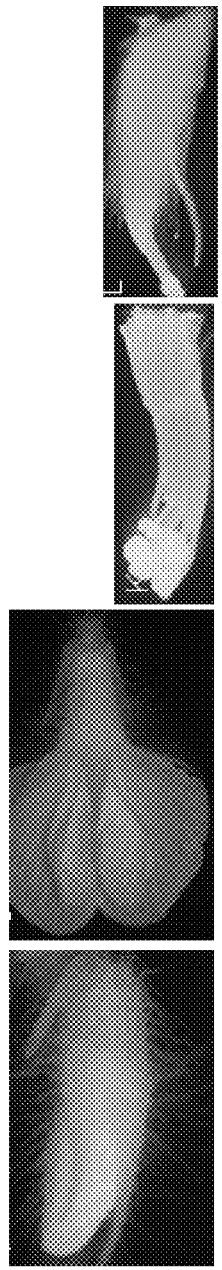
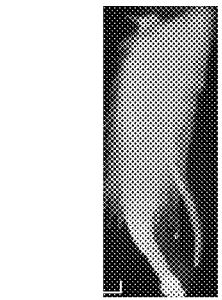
FIG. 7A  FIG. 7B  FIG. 7C  FIG. 7D  FIG. 7E  FIG. 7F  FIG. 7G  FIG. 7H  FIG. 7I  FIG. 7J  FIG. 7K  FIG. 7L

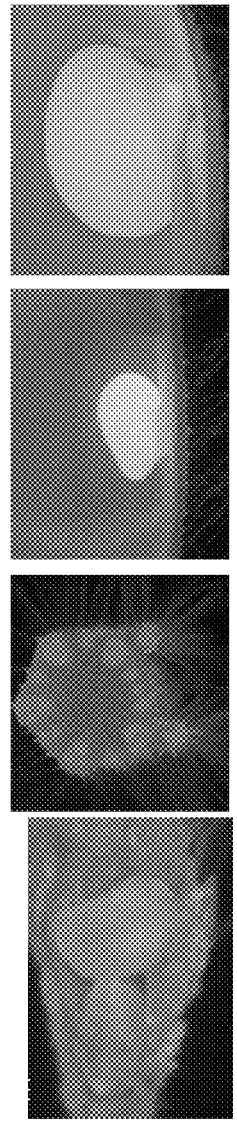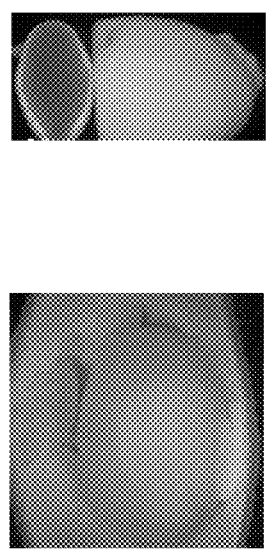
FIG. 7M  FIG. 7N  FIG. 7O  FIG. 7P
FIG. 7Q  FIG. 7R

SEQUENCE LISTING

```
<160> NUMBER OF SEQ ID NOS: 49

<210> SEQ ID NO 1
<211> LENGTH: 1502
<212> TYPE: DNA
<213> ORGANISM: Glycine max

<400> SEQUENCE: 1
gggtttactt attttgtggg tatctatact tttattagat ttttaatcag gctcctgatt      60 tcttttatt tcgattgaat tcctgaactt gtattattca gtagatcgaa taaattataa     120
aaagataaaa tcataaaata atattttatc ctatcaatca tattaaagca atgaatatgt     180
aaaattaatc ttatctttat tttaaaaaat catataggtt tagtattttt ttaaaaataa     240
agataggatt agttttacta ttcactgctt attacttta aaaaaatcat aaaggtttag     300
tattttttta aaataaatat aggaatagtt ttactattca ctgctttaat agaaaaatag     360
tttaaaattt aagatagttt taatcccagc atttgccacg tttgaacgtg agccgaaacg     420
atgtcgttac attatcttaa cctagctgaa acgatgtcgt cataatatcg ccaaatgcca     480
```

| | |
|---|---|
| actggactac gtcgaaccca caaatcccac aaagcgcgtg aaatcaaatc gctcaaacca | 540 |
| caaaaaagaa caacgcgttt gttacacgct caatcccacg cgagtagagc acagtaacct | 600 |
| tcaaataagc gaatggggca taatcagaaa tccgaaataa acctaggggc attatcggaa | 660 |
| atgaaaagta gctcactcaa tataaaaatc taggaaccct agttttcgtt atcactctgt | 720 |
| gctccctcgc tctatttctc agtctctgtg tttgcggctg aggattccga acgagtgacc | 780 |
| ttcttcgttt ctcgcaaagg taacagcctc tgctcttgtc tcttcgattc gatctatgcc | 840 |
| tgtctcttat ttacgatgat gtttcttcgg ttatgttttt ttatttatgc tttatgctgt | 900 |
| tgatgttcgg ttgtttgttt cgctttgttt tgtggttca gttttttagg attcttttgg | 960 |
| tttttgaatc gattaatcgg aagagatttt cgagttattt ggtgtgttgg aggtgaatct | 1020 |
| ttttttttgag gtcatagatc tgttgtattt gtgttataaa catgcgactt tgtatgattt | 1080 |
| tttacgaggt tatgatgttc tggttgtttt attatgaatc tgttgagaca gaaccatgat | 1140 |
| ttttgttgat gttcgtttac actattaaag gtttgtttta acaggattaa aagtttttta | 1200 |
| agcatgttga aggagtcttg tagatatgta accgtcgata gttttttttgt gggtttgttc | 1260 |
| acatgttatc aagcttaatc ttttactatg tatgcgacca tatctggatc cagcaaaggc | 1320 |
| gatttttttaa ttccttgtga aacttttgta atatgaagtt gaaattttgt tattggtaaa | 1380 |
| ctataaatgt gtgaagttgg agtataacctt taccttctta tttggctttg tgatagttta | 1440 |
| atttatatgt attttgagtt ctgacttgta tttctttgaa ttgattctag tttaagtaat | 1500 |
| cc | 1502 |

<210> SEQ ID NO 2
<211> LENGTH: 1184
<212> TYPE: DNA
<213> ORGANISM: Glycine max

<400> SEQUENCE: 2

| | |
|---|---|
| ataggaatag ttttactatt cactgcttta atagaaaaat agtttaaaat ttaagatagt | 60 |
| tttaatccca gcatttgcca cgtttgaacg tgagccgaaa cgatgtcgtt acattatctt | 120 |
| aacctagctg aaacgatgtc gtcataatat cgccaaatgc caactggact acgtcgaacc | 180 |
| cacaaatccc acaaagcgcg tgaaatcaaa tcgctcaaac cacaaaaaag aacaacgcgt | 240 |
| ttgttacacg ctcaatccca cgcgagtaga gcacagtaac cttcaaataa gcgaatgggg | 300 |
| cataatcaga atccgaaaat aaacctaggg gcattatcgg aaatgaaaag tagctcactc | 360 |
| aatataaaaa tctaggaacc ctagttttcg ttatcactct gtgctccctc gctctatttc | 420 |
| tcagtctctg tgtttgcggc tgaggattcc gaacgagtga ccttcttcgt ttctcgcaaa | 480 |
| ggtaacagcc tctgctcttg tctcttcgat tcgatctatg cctgtctctt atttacgatg | 540 |
| atgtttcttc ggttatgttt tttatttat gctttatgct gttgatgttc ggttgtttgt | 600 |
| ttcgctttgt tttgtggtt cagttttttta ggattcttttt ggtttttgaa tcgattaatc | 660 |
| ggaagagatt ttcgagttat tggtgtgtt ggaggtgaat cttttttttg aggtcataga | 720 |
| tctgttgtat ttgtgttata acatgcgac tttgtatgat ttttttacgag gttatgatgt | 780 |
| tctggttgtt ttattatgaa tctgttgaga cagaaccatg attttttgttg atgttcgttt | 840 |
| acactattaa aggtttgttt taacaggatt aaaagttttt taagcatgtt gaaggagtct | 900 |
| tgtagatatg taaccgtcga tagttttttt gtgggtttgt tcacatgtta tcaagcttaa | 960 |
| tcttttacta tgtatgcgac catatctgga tccagcaaag gcgattttttt aattccttgt | 1020 |
| gaaacttttg taatatgaag ttgaaatttttt gttattggta aactataaat gtgtgaagtt | 1080 |

```
ggagtatacc tttaccttct tatttggctt tgtgatagtt taatttatat gtattttgag    1140
ttctgacttg tatttctttg aattgattct agtttaagta atcc                     1184

<210> SEQ ID NO 3
<211> LENGTH: 924
<212> TYPE: DNA
<213> ORGANISM: Glycine max

<400> SEQUENCE: 3
cgcgagtaga gcacagtaac cttcaaataa gcgaatgggg cataatcaga aatccgaaat      60
aaacctaggg gcattatcgg aaatgaaaag tagctcactc aatataaaaa tctaggaacc     120
ctagttttcg ttatcactct gtgctccctc gctctatttc tcagtctctg tgtttgcggc     180
tgaggattcc gaacgagtga ccttcttcgt ttctcgcaaa ggtaacagcc tctgctcttg     240
tctcttcgat tcgatctatg cctgtctctt atttacgatg atgtttcttc ggttatgttt     300
ttttatttat gctttatgct gttgatgttc ggttgtttgt ttcgctttgt ttttgtggtt     360
cagtttttta ggattctttt ggttttgaa tcgattaatc ggaagagatt ttcgagttat      420
ttggtgtgtt ggaggtgaat cttttttttg aggtcataga tctgttgtat ttgtgttata    480
aacatgcgac tttgtatgat tttttacgag gttatgatgt tctggttgtt ttattatgaa    540
tctgttgaga cagaaccatg atttttgttg atgttcgttt acactattaa aggtttgttt    600
taacaggatt aaaagttttt taagcatgtt gaaggagtct tgtagatatg taaccgtcga    660
tagttttttt gtgggtttgt tcacatgtta tcaagcttaa tcttttacta tgtatgcgac    720
catatctgga tccagcaaag gcgattttttt aattccttgt gaacttttg taatatgaag    780 ttgaaatttt gttattggta aactataaat gtgtgaagtt ggagtatacc tttaccttct    840
tatttggctt tgtgatagtt taatttatat gtattttgag ttctgacttg tatttctttg    900
aattgattct agtttaagta atcc                                            924

<210> SEQ ID NO 4
<211> LENGTH: 682
<212> TYPE: DNA
<213> ORGANISM: Glycine max

<400> SEQUENCE: 4
tcttcgattc gatctatgcc tgtctcttat ttacgatgat gtttcttcgg ttatgttttt      60
ttatttatgc tttatgctgt tgatgttcgg ttgtttgttt cgctttgttt ttgtggttca    120
gttttttagg attcttttgg ttttgaatc gattaatcgg aagagatttt cgagttattt     180
ggtgtgttgg aggtgaatct ttttttgag gtcatagatc tgttgtattt gtgttataaa     240
catgcgactt tgtatgattt tttacgaggt tatgatgttc tggttgtttt attatgaatc    300
tgttgagaca gaaccatgat ttttgttgat gttcgtttac actattaaag gtttgtttta    360
acaggattaa aagttttta agcatgttga aggagtcttg tagatatgta accgtcgata     420 gttttttttgt gggtttgttc acatgttatc aagcttaatc ttttactatg tatgcgacca   480
tatctggatc cagcaaaggc gatttttttaa ttccttgtga acttttgta atatgaagtt    540 gaaattttgt tattggtaaa ctataaatgt gtgaagttgg agtataccctt taccttctta   600 tttggctttg tgatagttta atttatatgt attttgagtt ctgacttgta tttctttgaa    660
ttgattctag tttaagtaat cc                                              682

<210> SEQ ID NO 5
<211> LENGTH: 477
<212> TYPE: DNA
```

<213> ORGANISM: Glycine max

<400> SEQUENCE: 5

```
ttgaggtcat agatctgttg tatttgtgtt ataaacatgc gactttgtat gatttttac      60
gaggttatga tgttctggtt gttttattat gaatctgttg agacagaacc atgattttg     120
ttgatgttcg tttacactat taaaggtttg ttttaacagg attaaaagtt ttttaagcat    180
gttgaaggag tcttgtagat atgtaaccgt cgatagtttt tttgtgggtt tgttcacatg    240
ttatcaagct taatctttta ctatgtatgc gaccatatct ggatccagca aaggcgattt    300
tttaattcct tgtgaaactt ttgtaatatg aagttgaaat tttgttattg gtaaactata    360
aatgtgtgaa gttggagtat acctttacct tcttatttgg ctttgtgata gtttaattta    420
tatgtatttt gagttctgac ttgtatttct ttgaattgat tctagtttaa gtaatcc       477
```

<210> SEQ ID NO 6
<211> LENGTH: 253
<212> TYPE: DNA
<213> ORGANISM: Glycine max

<400> SEQUENCE: 6

```
tgggtttgtt cacatgttat caagcttaat cttttactat gtatgcgacc atatctggat     60
ccagcaaagg cgatttttta attccttgtg aaacttttgt aatatgaagt tgaaattttg    120
ttattggtaa actataaatg tgtgaagttg gagtatacct ttaccttctt atttggcttt    180
gtgatagttt aatttatatg tattttgagt tctgacttgt atttctttga attgattcta    240
gtttaagtaa tcc                                                       253
```

<210> SEQ ID NO 7
<211> LENGTH: 38
<212> TYPE: DNA
<213> ORGANISM: artificial sequence
<220> FEATURE:
<223> OTHER INFORMATION: primer

<400> SEQUENCE: 7

```
ataatcccgg gctaatcgag ctggtactaa actaatgc                             38
```

<210> SEQ ID NO 8
<211> LENGTH: 34
<212> TYPE: DNA
<213> ORGANISM: artificial sequence
<220> FEATURE:
<223> OTHER INFORMATION: primer

<400> SEQUENCE: 8

```
tgattccatg gttctcctcg cctgggattc tttc                                 34
```

<210> SEQ ID NO 9
<211> LENGTH: 31
<212> TYPE: DNA
<213> ORGANISM: artificial sequence
<220> FEATURE:
<223> OTHER INFORMATION: primer

<400> SEQUENCE: 9

```
ggattactta aactagaatc aattcaaaga a                                    31
```

<210> SEQ ID NO 10
<211> LENGTH: 34
<212> TYPE: DNA
<213> ORGANISM: artificial sequence
<220> FEATURE:

<223> OTHER INFORMATION: primer

<400> SEQUENCE: 10
ataggaatag ttttactatt cactgcttta atag                              34

<210> SEQ ID NO 11
<211> LENGTH: 24
<212> TYPE: DNA
<213> ORGANISM: artificial sequence
<220> FEATURE:
<223> OTHER INFORMATION: primer

<400> SEQUENCE: 11
cgcgagtaga gcacagtaac cttc                                         24

<210> SEQ ID NO 12
<211> LENGTH: 24
<212> TYPE: DNA
<213> ORGANISM: artificial sequence
<220> FEATURE:
<223> OTHER INFORMATION: primer

<400> SEQUENCE: 12
tcttcgattc gatctatgcc tgtc                                         24

<210> SEQ ID NO 13
<211> LENGTH: 30
<212> TYPE: DNA
<213> ORGANISM: artificial sequence
<220> FEATURE:
<223> OTHER INFORMATION: primer

<400> SEQUENCE: 13
ttgaggtcat agatctgttg tatttgtgtt                                   30

<210> SEQ ID NO 14
<211> LENGTH: 25
<212> TYPE: DNA
<213> ORGANISM: artificial sequence
<220> FEATURE:
<223> OTHER INFORMATION: primer

<400> SEQUENCE: 14
tgggtttgtt cacatgttat caagc                                        25

<210> SEQ ID NO 15
<211> LENGTH: 691
<212> TYPE: DNA
<213> ORGANISM: Glycine max

<400> SEQUENCE: 15
gtaacagcct ctgctcttgt tcttcgatt cgatctatgc ctgtctctta tttacgatga    60
tgtttcttcg gttatgtttt tttatttatg ctttatgctg ttgatgttcg gttgtttgtt   120
tcgctttgtt tttgtggttc agttttttag gattcttttg gttttttgaat cgattaatcg  180 gaagagattt tcgagttatt tggtgtgttg gaggtgaatc ttttttttga ggtcatagat   240
ctgttgtatt tgtgttataa acatgcgact ttgtatgatt ttttacgagg ttatgatgtt   300
ctggttgttt tattatgaat ctgttgagac agaaccatga ttttttgttga tgttcgttta   360 cactattaaa ggtttgtttt aacaggatta aaagtttttt aagcatgttg aaggagtctt   420
gtagatatgt aaccgtcgat agttttttg tgggtttgtt cacatgttat caagcttaat    480 ctttactat gtatgcgacc atatctggat ccagcaaagg cgattttta attccttgtg     540

```
aaacttttgt aatatgaagt tgaaattttg ttattggtaa actataaatg tgtgaagttg      600
gagtatacct ttaccttctt atttggcttt gtgatagttt aatttatatg tattttgagt      660
tctgacttgt atttctttga attgattcta g                                     691

<210> SEQ ID NO 16
<211> LENGTH: 75
<212> TYPE: DNA
<213> ORGANISM: Glycine max

<400> SEQUENCE: 16
cctcgctcta tttctcagtc tctgtgtttg cggctgagga ttccgaacga gtgaccttct      60
tcgtttctcg caaag                                                      75

<210> SEQ ID NO 17
<211> LENGTH: 12
<212> TYPE: DNA
<213> ORGANISM: artificial sequence
<220> FEATURE:
<223> OTHER INFORMATION: putative 5'untranslated region

<400> SEQUENCE: 17
tttaagtaat cc                                                         12

<210> SEQ ID NO 18
<211> LENGTH: 1778
<212> TYPE: DNA
<213> ORGANISM: Glycine max

<400> SEQUENCE: 18
cacgagcctc gctctatttc tcagtctctg tgtttgcggc tgaggattcc gaacgagtga      60
ccttcttcgt ttctcgcaaa gtttaagtaa tcatgggtaa ggaaaaggtt cacatcaaca     120
ttgtcgtcat tggacatgtc gactctggga agtcaactac cactggtcac ttgatctaca     180
agcttggagg tattgacaag cgtgtgattg agaggttcga gaaggaggct gccgagatga     240
acaagaggtc attcaagtat gcctgggtgc tcgacaagct caaagctgag cgtgaaagag     300
gaattaccat tgatattgct ttgtggaagt ttgaaaccac caagtactac tgcacggtca     360
ttgatgctcc tggacatcgt gactttatca agaacatgat tactggtacc tcccaggccg     420
actgtgctgt ccttattatt gactccacca ctggtggttt tgaagctggt atttctaagg     480
atggacagac ccgtgagcat gctcttcttg ctttcaccct aggtgtgaag cagatgatct     540
gttgctgtaa caagatggat gccactaccc ccaagtactc taaggctagg tatgatgaaa     600
tcgtgaagga agtctcttct tacttgaaga aggttggtta caacccagac aagattccct     660 tgttcccat ctctggtttt gagggtgaca acatgattga gagtccacc aaccttgact        720 ggtacaaggg accaactctc cttgaggctc ttgaccaaat caatgagccc aagaggccct     780
ccgacaagcc tctaaggctt ccattgcagg atgtctacaa gattggtggt attggtactg     840
tgccagtggg acgtgtagag actggggttg tgaagcctgg tatggtggtg acttttggtc     900
ccactgggct gacaactgag gttaagtctg ttgagatgca ccatgaggct ctcacagagg     960
ctcttccagg tgacaatgtt ggatttaatg tgaagaatgt tgcagtcaag gatctcaagc    1020
gtggttttgt tgcatccaac tccaaggacg accctgccaa ggaagctgcc aacttcacat    1080
cccaagtcat tatcatgaac catcctggcc agattggtaa tggatacgca ccagtccttg    1140
actgccacac ttctcacatt gctgtgaagt ttctgaaaat cttgaccaag attgacaggc    1200
gatctggtaa ggagcttgag aaggagccca aattttgaa gaatggtgat gctggtatgg     1260
```

-continued

```
ttaagatggt tccaaccaag cccatggtgg ttgaaacttt ctctgagtat cctcccttg     1320 gtcgttttgc tgtgagggac atgcgtcaga ccgtagctgt tggagtcatc aagagtgttg    1380
agaagaaaga ccccaccgga gccaaggtca caaaggctgc cgccaagaag aagtgattgc    1440
attttggcaa ttttgctagc acatgtgatc atcaacgtgg tttcaaaaaa acttgttcct    1500
ttacagtagt ttatctttgc agagtcttag gtgtttgttt taccagttat attttgaagt    1560
gtccgccgat tcatgtagc cgtagccttc aaaactgggt tcttgatcgg cggtaacatt     1620
ttcgttgctg tttgtttttg atgagtactg ttttttgttt tgatggtaaa agtctgagat    1680
tttcaaattc acaagcagcc atagggtttt agtccattc ctttgctgct gaggagggat     1740
gtcttaaatt tgcatttaat ttataaggaa gttttgtt                             1778
```

<210> SEQ ID NO 19
<211> LENGTH: 447
<212> TYPE: PRT
<213> ORGANISM: Glycine max

<400> SEQUENCE: 19

```
Met Gly Lys Glu Lys Val His Ile Asn Ile Val Ile Gly His Val
1               5                   10                  15

Asp Ser Gly Lys Ser Thr Thr Thr Gly His Leu Ile Tyr Lys Leu Gly
            20                  25                  30

Gly Ile Asp Lys Arg Val Ile Glu Arg Phe Glu Lys Glu Ala Ala Glu
        35                  40                  45

Met Asn Lys Arg Ser Phe Lys Tyr Ala Trp Val Leu Asp Lys Leu Lys
    50                  55                  60

Ala Glu Arg Glu Arg Gly Ile Thr Ile Asp Ile Ala Leu Trp Lys Phe
65                  70                  75                  80

Glu Thr Thr Lys Tyr Tyr Cys Thr Val Ile Asp Ala Pro Gly His Arg
                85                  90                  95

Asp Phe Ile Lys Asn Met Ile Thr Gly Thr Ser Gln Ala Asp Cys Ala
            100                 105                 110

Val Leu Ile Ile Asp Ser Thr Thr Gly Gly Phe Glu Ala Gly Ile Ser
        115                 120                 125

Lys Asp Gly Gln Thr Arg Glu His Ala Leu Leu Ala Phe Thr Leu Gly
    130                 135                 140

Val Lys Gln Met Ile Cys Cys Cys Asn Lys Met Asp Ala Thr Thr Pro
145                 150                 155                 160

Lys Tyr Ser Lys Ala Arg Tyr Asp Glu Ile Val Lys Glu Val Ser Ser
                165                 170                 175

Tyr Leu Lys Lys Val Gly Tyr Asn Pro Asp Lys Ile Pro Phe Val Pro
            180                 185                 190

Ile Ser Gly Phe Glu Gly Asp Asn Met Ile Glu Arg Ser Thr Asn Leu
        195                 200                 205

Asp Trp Tyr Lys Gly Pro Thr Leu Leu Glu Ala Leu Asp Gln Ile Asn
    210                 215                 220

Glu Pro Lys Arg Pro Ser Asp Lys Pro Leu Arg Leu Pro Leu Gln Asp
225                 230                 235                 240

Val Tyr Lys Ile Gly Gly Ile Gly Thr Val Pro Val Gly Arg Val Glu
                245                 250                 255

Thr Gly Val Val Lys Pro Gly Met Val Val Thr Phe Gly Pro Thr Gly
            260                 265                 270

Leu Thr Thr Glu Val Lys Ser Val Glu Met His His Glu Ala Leu Thr
        275                 280                 285
```

```
Glu Ala Leu Pro Gly Asp Asn Val Gly Phe Asn Val Lys Asn Val Ala
            290                 295                 300

Val Lys Asp Leu Lys Arg Gly Phe Val Ala Ser Asn Ser Lys Asp Asp
305                 310                 315                 320

Pro Ala Lys Glu Ala Ala Asn Phe Thr Ser Gln Val Ile Ile Met Asn
                325                 330                 335

His Pro Gly Gln Ile Gly Asn Gly Tyr Ala Pro Val Leu Asp Cys His
            340                 345                 350

Thr Ser His Ile Ala Val Lys Phe Ser Glu Ile Leu Thr Lys Ile Asp
        355                 360                 365

Arg Arg Ser Gly Lys Glu Leu Glu Lys Glu Pro Lys Phe Leu Lys Asn
    370                 375                 380

Gly Asp Ala Gly Met Val Lys Met Val Pro Thr Lys Pro Met Val Val
385                 390                 395                 400

Glu Thr Phe Ser Glu Tyr Pro Pro Leu Gly Arg Phe Ala Val Arg Asp
                405                 410                 415

Met Arg Gln Thr Val Ala Val Gly Val Ile Lys Ser Val Glu Lys Lys
            420                 425                 430

Asp Pro Thr Gly Ala Lys Val Thr Lys Ala Ala Ala Lys Lys Lys
        435                 440                 445

<210> SEQ ID NO 20
<211> LENGTH: 4786
<212> TYPE: DNA
<213> ORGANISM: artificial sequence
<220> FEATURE:
<223> OTHER INFORMATION: gateway entry construct

<400> SEQUENCE: 20
ccgggtttac ttattttgtg ggtatctata cttttattag atttttaatc aggctcctga      60
tttcttttta tttcgattga attcctgaac ttgtattatt cagtagatcg aataaattat     120
aaaaagataa aatcataaaa taatatttta tcctatcaat catattaaag caatgaatat     180
gtaaaattaa tcttatcttt attttaaaaa atcatatagg tttagtattt ttttaaaaat     240
aaagatagga ttagttttac tattcactgc ttattacttt taaaaaaatc ataaaggttt     300 agtattttt taaaataaat ataggaatag ttttactatt cactgcttta atagaaaaat     360
agtttaaaat ttaagatagt tttaatccca gcatttgcca cgtttgaacg tgagccgaaa     420
cgatgtcgtt acattatctt aacctagctg aaacgatgtc gtcataatat cgccaaatgc     480
caactggact acgtcgaacc cacaaatccc acaaagcgcg tgaaatcaaa tcgctcaaac     540
cacaaaaaag aacaacgcgt tgttacacg ctcaatccca cgcgagtaga gcacagtaac     600
cttcaaataa gcgaatgggg cataatcaga aatccgaaat aaacctaggg gcattatcgg     660
aaatgaaaag tagctcactc aatataaaaa tctaggaacc ctagttttcg ttatcactct     720
gtgctccctc gctctatttc tcagtctctg tgtttgcggc tgaggattcc gaacgagtga     780
ccttcttcgt ttctcgcaaa ggtaacagcc tctgctcttg tctcttcgat tcgatctatg     840
cctgtctctt atttacgatg atgtttcttc ggttatgttt ttttatttat gctttatgct     900
gttgatgttc ggttgtttgt ttcgctttgt ttttgtggtt cagttttta ggattctttt     960 ggtttttgaa tcgattaatc ggaagagatt ttcgagttat ttggtgtgtt ggaggtgaat    1020 ctttttttg aggtcataga tctgttgtat ttgtgttata acatgcgac tttgtatgat    1080 tttttacgag gttatgatgt tctggttgtt ttattatgaa tctgttgaga cagaaccatg    1140 attttttgttg atgttcgttt acactattaa aggtttgttt taacaggatt aaaagttttt    1200
```

-continued

```
taagcatgtt gaaggagtct tgtagatatg taaccgtcga tagttttttt gtgggtttgt    1260
tcacatgtta tcaagcttaa tcttttacta tgtatgcgac catatctgga tccagcaaag    1320
gcgattttt  aattccttgt gaaacttttg taatatgaag ttgaaatttt gttattggta    1380
aactataaat gtgtgaagtt ggagtatacc tttaccttct tatttggctt tgtgatagtt    1440
taatttatat gtattttgag ttctgacttg tatttctttg aattgattct agtttaagta    1500
atccatggcc cacagcaagc acggcctgaa ggaggagatg accatgaagt accacatgga    1560
gggctgcgtg aacggccaca agttcgtgat caccggcgag ggcatcggct acccctccaa    1620
gggcaagcag accatcaacc tgtgcgtgat cgagggcggc cccctgccct tcagcgagga    1680
catcctgagc gccggcttca gtacggcga  ccggatcttc accgagtacc cccaggacat    1740
cgtggactac ttcaagaaca gctgccccgc cggctacacc tggggccgga gcttcctgtt    1800
cgaggacggc gccgtgtgca tctgtaacgt ggacatcacc gtgagcgtga aggagaactg    1860
catctaccac aagagcatct tcaacggcgt gaacttcccc gccgacgcc  ccgtgatgaa    1920
gaagatgacc accaactggg aggccagctg cgagaagatc atgcccgtgc ctaagcaggg    1980
catcctgaag ggcgacgtga gcatgtacct gctgctgaag gacggcggcc ggtaccggtg    2040
ccagttcgac accgtgtaca aggccaagag cgtgcccagc aagatgcccg agtggcactt    2100
catccagcac aagctgctgc gggaggaccg gagcgacgcc aagaaccaga gtgcagct     2160
gaccgagcac gccatcgcct tccccagcgc cctggcctga gagctcgaat tccccgatc    2220
gttcaaacat ttggcaataa agtttcttaa gattgaatcc tgttgccggt cttgcgatga    2280
ttatcatata atttctgttg aattacgtta agcatgtaat aattaacatg taatgcatga    2340
cgttatttat gagatgggtt tttatgatta gagtcccgca attatacatt taatacgcga    2400
tagaaaacaa aatatagcgc gcaaactagg ataaattatc gcgcgcggtg tcatctatgt    2460
tactagatcg ggaattctag tggccggcc  agctgatatc catcacactg gcggccgcac    2520
tcgactgaat tggttccggc gccagcctgc ttttttgtac aaagttggca ttataaaaaa    2580
gcattgctta tcaattttgtt gcaacgaaca ggtcactatc agtcaaaata aaatcattat    2640
ttggggcccg agcttaagta actaactaac aggaagagtt tgtagaaacg caaaaaggcc    2700
atccgtcagg atggccttct gcttagtttg atgcctggca gtttatggcg ggcgtcctgc    2760
ccgcccacct ccgggccgtt gcttcacaac gttcaaatcc gctcccggcg gatttgtcct    2820
actcaggaga gcgttcaccg acaaacaaca gataaaacga aaggcccagt cttccgactg    2880
agcctttcgt tttatttgat gcctggcagt tccctactct cgcttagtag ttagacgtcc    2940
ccgagatcca tgctagcggt aatacggtta tccacagaat caggggataa cgcaggaaag    3000
aacatgtgag caaaaggcca gcaaaaggcc aggaaccgta aaaaggccgc gttgctggcg    3060
ttttttccata ggctccgccc cctgacgag  catcacaaaa atcgacgctc aagtcagagg    3120
tggcgaaacc cgacaggact ataaagatac caggcgtttc cccctggaag ctccctcgtg    3180
cgctctcctg ttccgaccct gccgcttacc ggatacctgt ccgcctttct cccttcggga    3240
agcgtggcgc tttctcatag ctcacgctgt aggtatctca gttcggtgta ggtcgttcgc    3300
tccaagctgg gctgtgtgca cgaaccccc  gttcagcccg accgctgcgc cttatccggt    3360
aactatcgtc ttgagtccaa cccggtaaga cacgacttat cgccactggc agcagccact    3420
ggtaacagga ttagcagagc gaggtatgta ggcggtgcta cagagttctt gaagtggtgg    3480
cctaactacg gctacactag aagaacagta tttggtatct gcgctctgct gaagccagtt    3540
accttcggaa aaagagttgg tagctcttga tccggcaaac aaaccaccgc tggtagcggt    3600
```

```
ggtttttttg tttgcaagca gcagattacg cgcagaaaaa aaggatctca agaagatcct    3660
ttgatctttt ctacggggtc tgacgctcag tggaacgggg cccaatctga ataatgttac    3720
aaccaattaa ccaattctga ttagaaaaac tcatcgagca tcaaatgaaa ctgcaattta    3780
ttcatatcag gattatcaat accatatttt tgaaaaagcc gtttctgtaa tgaaggagaa    3840
aactcaccga ggcagttcca taggatggca agatcctggt atcggtctgc gattccgact    3900
cgtccaacat caatacaacc tattaatttc ccctcgtcaa aaataaggtt atcaagtgag    3960
aaatcaccat gagtgacgac tgaatccggt gagaatggca aaagtttatg catttctttc    4020
cagacttgtt caacaggcca gccattacgc tcgtcatcaa aatcactcgc atcaaccaaa    4080
ccgttattca ttcgtgattg cgcctgagcg agacgaaata cgcgatcgct gttaaaagga    4140
caattacaaa caggaatcga atgcaaccgg cgcaggaaca ctgccagcgc atcaacaata    4200
ttttcacctg aatcaggata ttcttctaat acctggaatg ctgttttttcc ggggatcgca    4260 gtggtgagta accatgcatc atcaggagta cggataaaat gcttgatggt cggaagaggc    4320
ataaattccg tcagccagtt tagtctgacc atctcatctg taacatcatt ggcaacgcta    4380
cctttgccat gtttcagaaa caactctggc gcatcgggct tcccatacaa gcgatagatt    4440
gtcgcacctg attgcccgac attatcgcga gcccatttat acccatataa atcagcatcc    4500
atgttggaat ttaatcgcgg cctcgacgtt tcccgttgaa tatggctcat aacacccctt    4560
gtattactgt ttatgtaagc agacagtttt attgttcatg atgatatatt tttatcttgt    4620
gcaatgtaac atcagagatt ttgagacacg gccagagct gcagctggat ggcaaataat    4680 gatttattt tgactgatag tgacctgttc gttgcaacaa attgataagc aatgctttct    4740
tataatgcca actttgtaca agaaagctgg gtctagatat ctcgac    4786
```

<210> SEQ ID NO 21
<211> LENGTH: 9311
<212> TYPE: DNA
<213> ORGANISM: artificial sequence
<220> FEATURE:
<223> OTHER INFORMATION: vector
<400> SEQUENCE: 21

```
tttgtacaaa cttgttgatg gggttaacat atcataactt cgtataatgt atgctatacg     60
aagttatagg cctggatctt cgaggtcgag cggccgcaga tttaggtgac actatagaat    120
atgcatcact agtaagcttt gctctagatc aaactcacat ccaaacataa catggatatc    180
ttccttacca atcatactaa ttattttggg ttaaatatta atcattattt ttaagatatt    240
aattaagaaa ttaaaagatt ttttaaaaaa atgtataaaa ttatattatt catgattttt    300
catacatttg attttgataa taatatatt ttttttaatt tcttaaaaaa tgttgcaaga    360 cactattag acatagtctt gttctgttta caaaagcatt catcatttaa tacattaaaa    420
aatatttaat actaacagta gaatcttctt gtgagtggtg tgggagtagg caacctggca    480
ttgaaacgag agaaagagag tcagaaccag aagacaaata aaaagtatgc aacaaacaaa    540
tcaaaatcaa agggcaaagg ctggggttgg ctcaattggt tgctacattc aattttcaac    600
tcagtcaacg gttgagattc actctgactt ccccaatcta agccgcggat gcaaacggtt    660
gaatctaacc cacaatccaa tctcgttact tagggctttt ccgtcatta actcaccct     720 gccaccgt ttccctataa attggaactc aatgctcccc tctaaactcg tatcgcttca    780
gagttgagac caagacacac tcgttcatat atctctctgc tcttctcttc tcttctacct    840
ctcaaggtac ttttcttctc cctctaccaa atcctagatt ccgtggttca atttcggatc    900
```

```
ttgcacttct ggtttgcttt gccttgcttt ttcctcaact gggtccatct aggatccatg    960
tgaaactcta ctcttcttt aatatctgcg gaatacgcgt ttgactttca gatctagtcg   1020
aaatcatttc ataattgcct ttctttcttt tagcttatga gaataaaat cactttttt    1080 ttatttcaaa ataaaccttg ggccttgtgc tgactgagat ggggtttggt gattacagaa   1140
ttttagcgaa ttttgtaatt gtacttgttt gtctgtagtt ttgttttgtt ttcttgtttc   1200
tcatacattc cttaggcttc aattttattc gagtataggt cacaataggaa attcaaactt   1260 tgagcagggg aattaatccc ttccttcaaa tccagtttgt ttgtatatat gtttaaaaaaa  1320 tgaaactttt gctttaaatt ctattataac ttttttttatg gctgaaattt ttgcatgtgt   1380
ctttgctctc tgttgtaaat ttactgtttta ggtactaact ctaggcttgt tgtgcagttt   1440
ttgaagtata accatgccac acaacacaat ggcggccacc gcttccagaa ccacccgatt   1500
ctcttcttcc tcttcacacc ccaccttccc caaacgcatt actagatcca ccctccctct   1560
ctctcatcaa accctcacca aacccaacca cgctctcaaa atcaaatgtt ccatctccaa   1620 acccccacg gcggcgccct tcaccaagga agcgccgacc acggagccct tcgtgtcacg   1680
gttcgcctcc ggcgaacctc gcaagggcgc ggacatcctt gtggaggcgc tggagaggca   1740
gggcgtgacg acggtgttcg cgtaccccgg cggtgcgtcg atggagatcc accaggcgct   1800
cacgcgctcc gccgccatcc gcaacgtgct cccgcgccac gagcagggcg gcgtcttcgc   1860
cgccgaaggc tacgcgcgtt cctccggcct ccccggcgtc tgcattgcca cctccggccc   1920
cggcgccacc aacctcgtga gcggcctcgc cgacgcttta atggacagcg tcccagtcgt   1980
cgccatcacc ggccaggtcg cccgccggat gatcggcacc gacgccttcc aagaaacccc   2040
gatcgtggag gtgagcagat ccatcacgaa gcacaactac ctcatcctcg acgtcgacga   2100
catcccccgc gtcgtcgccg aggctttctt cgtcgccacc tccggccgcc ccggtccggt   2160
cctcatcgac attcccaaag acgttcagca gcaactcgcc gtgcctaatt gggacgagcc   2220
cgttaacctc cccggttacc tcgccaggct gcccaggccc ccgccgagg cccaattgga   2280 acacattgtc agactcatca tggaggccca aaagcccgtt ctctacgtcg gcggtggcag   2340
tttgaattcc agtgctgaat tgaggcgctt tgttgaactc actggtattc ccgttgctag   2400
cactttaatg ggtcttggaa cttttcctat tggtgatgaa tattcccttc agatgctggg   2460
tatgcatggt actgtttatg ctaactatgc tgttgacaat agtgatttgt tgcttgcctt   2520 tgggtaagg tttgatgacc gtgttactgg gaagcttgag gcttttgcta gtagggctaa   2580
gattgttcac attgatattg attctgccga gattgggaag aacaagcagg cgcacgtgtc   2640
ggtttgcgcg gatttgaagt tggccttgaa gggaattaat atgatttgg aggagaaagg   2700 agtggagggt aagtttgatc ttggaggttg gagagaagag attaatgtgc agaaacacaa   2760
gtttccattg ggttacaaga cattccagga cgcgatttct ccgcagcatg ctatcgaggt   2820
tcttgatgag ttgactaatg gagatgctat tgttagtact ggggttgggc agcatcaaat   2880
gtgggctgcg cagttttaca gtacaagag accgaggcag tggttgacct caggggggtct    2940 tggagccatg ggttttggat tgcctgcggc tattggtgct gctgttgcta accctggggc   3000
tgttgtggtt gacattgatg gggatggtag tttcatcatg aatgttcagg agttggccac   3060
tataagagtg gagaatctcc cagttaagat attgttgttg aacaatcagc atttgggtat   3120
ggtggttcag ttggaggata ggttctacaa gtccaataga gctcacacct atcttggaga   3180
tccgtctagc gagagcgaga tattcccaaa catgctcaag tttgctgatg cttgtgggat   3240
accggcagcg cgagtgacga agaaggaaga gcttagagcg gcaattcaga gaatgttgga   3300
```

```
caccccctggc ccctaccttc ttgatgtcat tgtgccccat caggagcatg tgttgccgat    3360
gattcccagt aatggatcct tcaaggatgt gataactgag ggtgatggta gaacgaggta    3420
ctgattgcct agaccaaatg ttccttgatg cttgttttgt acaatatata aagataatg     3480
ctgtcctagt tgcaggattt ggcctgtggt gagcatcata gtctgtagta gttttggtag    3540
caagacattt tattttcctt ttatttaact tactacatgc agtagcatct atctatctct    3600
gtagtctgat atctcctgtt gtctgtattg tgccgttgga ttttttgctg tagtgagact    3660
gaaaatgatg tgctagtaat aatatttctg ttagaaatct aagtagagaa tctgttgaag    3720
aagtcaaaag ctaatggaat caggttacat attcaatgtt tttctttttt tagcggttgg    3780
tagacgtgta gattcaactt ctcttggagc tcacctaggc aatcagtaaa atgcatattc    3840
cttttttaac ttgccattta tttacttttta gtggaaattg tgaccaattt gttcatgtag    3900
aacggatttg gaccattgcg tccacaaaac gtctcttttg ctcgatcttc acaaagcgat    3960
accgaaatcc agagatagtt ttcaaaagtc agaaatggca aagttataaa tagtaaaaca    4020
gaatagatgc tgtaatcgac ttcaataaca agtggcatca cgtttctagt tctagaccca    4080
tcagatcgaa ttaacatatc ataacttcgt ataatgtatg ctatacgaag ttataggcct    4140
ggatccacta gttctagagc ggccgctcga ggggggggccc ggtaccggcg cgccgttcta    4200
tagtgtcacc taaatcgtat gtgtatgata cataaggtta tgtattaatt gtagccgcgt    4260
tctaacgaca atatgtccat atggtgcact ctcagtacaa tctgctctga tgccgcatag    4320
ttaagccagc cccgacaccc gccaacaccc gctgacgcgc cctgacgggc ttgtctgctc    4380
ccggcatccg cttacagaca agctgtgacc gtctccggga gctgcatgtg tcagaggttt    4440
tcaccgtcat caccgaaacg cgcgagacga aagggcctcg tgatacgcct attttttatag   4500
gttaatgtca tgaccaaaat cccttaacgt gagttttcgt tccactgagc gtcagacccc    4560
gtagaaaaga tcaaaggatc ttcttgagat cctttttttc tgcgcgtaat ctgctgcttg    4620
caaacaaaaa aaccaccgct accagcggtg gtttgtttgc cggatcaaga gctaccaact    4680
ctttttccga aggtaactgg cttcagcaga gcgcagatac caaatactgt ccttctagtg    4740
tagccgtagt taggccacca cttcaagaac tctgtagcac cgcctacata cctcgctctg    4800
ctaatcctgt taccagtggc tgctgccagt ggcgataagt cgtgtcttac cgggttggac    4860
tcaagacgat agttaccgga taaggcgcag cggtcgggct gaacggggg ttcgtgcaca     4920
cagcccagct tggagcgaac gacctacacc gaactgagat acctacagcg tgagcattga    4980
gaaagcgcca cgcttcccga agggagaaag gcggacaggt atccggtaag cggcagggtc    5040
ggaacaggag agcgcacgag ggagcttcca gggggaaacg cctggtatct ttatagtcct    5100
gtcgggtttc gccacctctg acttgagcgt cgatttttgt gatgctcgtc aggggggcgg    5160
agcctatgga aaaacgccag caacgcggcc ttttttacggt tcctggcctt tgctggcct    5220
tttgctcaca tgttctttcc tgcgttatcc cctgattctg tggataaccg tattaccgcc    5280
tttgagtgag ctgataccgc tcgccgcagc cgaacgaccg agcgcagcga gtcagtgagc    5340
gaggaagcgg aagagcgccc aatacgcaaa ccgcctctcc ccgcgcgttg gccgattcat    5400
taatgcaggt tgatcagatc tcgatcccgc gaaattaata cgactcacta tagggagacc    5460
acaacggttt ccctctagaa ataattttgt ttaactttaa gaaggagata tacccatgga    5520
aaagcctgaa ctcaccgcga cgtctgtcga agtttctgat cgaaaagt tcgacagcgt      5580
ctccgacctg atgcagctct cggagggcga agaatctcgt gctttcagct tcgatgtagg    5640
agggcgtgga tatgtcctgc gggtaaatag ctgcgccgat ggtttctaca aagatcgtta    5700
```

```
tgtttatcgg cactttgcat cggccgcgct cccgattccg aagtgcttg acattgggga      5760
attcagcgag agcctgacct attgcatctc ccgccgtgca cagggtgtca cgttgcaaga      5820
cctgcctgaa accgaactgc ccgctgttct gcagccggtc gcggaggcta tggatgcgat      5880
cgctgcggcc gatcttagcc agacgagcgg gttcggccca ttcggaccgc aaggaatcgg      5940
tcaatacact acatggcgtg atttcatatg cgcgattgct gatccccatg tgtatcactg      6000
gcaaactgtg atggacgaca ccgtcagtgc gtccgtcgcg caggctctcg atgagctgat      6060
gctttgggcc gaggactgcc ccgaagtccg gcacctcgtg cacgcggatt cggctccaa       6120
caatgtcctg acgacaatg gccgcataac agcggtcatt gactggagcg aggcgatgtt       6180
cggggattcc caatacgagg tcgccaacat cttcttctgg aggccgtggt tggcttgtat      6240
ggagcagcag acgcgctact tcgagcggag gcatccggag cttgcaggat cgccgcggct      6300
ccgggcgtat atgctccgca ttggtcttga ccaactctat cagagcttgg ttgacggcaa      6360
tttcgatgat gcagcttggg cgcagggtcg atgcgacgca atcgtccgat ccggagccgg      6420
gactgtcggg cgtacacaaa tcgcccgcag aagcgcggcc gtctggaccg atggctgtgt      6480
agaagtactc gccgatagtg gaaaccgacg ccccagcact cgtccgaggg caaaggaata      6540
gtgaggtaca gcttggatcg atccggctgc taacaaagcc cgaaaggaag ctgagttggc      6600
tgctgccacc gctgagcaat aactagcata accccttggg gcctctaaac gggtcttgag      6660
gggttttttg ctgaaaggag gaactatatc cggatgatcg ggcgcgccgg tacccatcaa      6720
ccactttgta caagaaagct gggtctagat atctcgaccc gggtttactt attttgtggg      6780
tatctatact tttattagat ttttaatcag gctcctgatt tctttttatt tcgattgaat      6840
tcctgaactt gtattattca gtagatcgaa taaattataa aaagataaaa tcataaaata      6900
atattttatc ctatcaatca tattaaagca atgaatatgt aaaattaatc ttatctttat      6960
tttaaaaaat catataggtt tagtattttt ttaaaaataa agataggatt agttttacta      7020
ttcactgctt attactttta aaaaaatcat aaaggtttag tattttttta aaataaatat      7080
aggaatagtt ttactattca ctgctttaat agaaaaatag tttaaaattt aagatagttt      7140
taatcccagc atttgccacg tttgaacgtg agccgaaacg atgtcgttac attatcttaa      7200
cctagctgaa acgatgtcgt cataatatcg ccaaatgcca actggactac gtcgaaccca      7260
caaatcccac aaagcgcgtg aaatcaaatc gctcaaacca caaaaagaa caacgcgttt       7320
gttacacgct caatcccacg cgagtagagc acagtaacct tcaaataagc gaatggggca      7380
taatcagaaa tccgaaataa acctaggggc attatcggaa atgaaaagta gctcactcaa      7440
tataaaaatc taggaaccct agttttcgtt atcactctgt gctccctcgc tctatttctc      7500
agtctctgtg tttgcggctg aggattccga acgagtgacc ttcttcgttt ctcgcaaagg      7560
taacagcctc tgctcttgtc tcttcgattc gatctatgcc tgtctcttat ttacgatgat      7620
gtttcttcgg ttatgttttt ttatttatgc tttatgctgt tgatgttcgg ttgtttgttt      7680
cgctttgttt ttgtggttca gttttttagg attcttttgg ttttttgaatc gattaatcgg     7740
aagagatttt cgagttattt ggtgtgttgg aggtgaatct ttttttttgag gtcatagatc      7800
tgttgtattt gtgttataaa catgcgactt tgtatgattt tttacgaggt tatgatgttc       7860
tggttgtttt attatgaatc tgttgagaca gaaccatgat ttttgttgat gttcgtttac      7920
actattaaag gtttgtttta acaggattaa aagttttta agcatgttga aggagtcttg       7980
tagatatgta accgtcgata gttttttttgt gggtttgttc acatgttatc aagcttaatc     8040
ttttactatg tatgcgacca tatctggatc cagcaaaggc gatttttaa ttccttgtga       8100
```

```
aacttttgta atatgaagtt gaaattttgt tattggtaaa ctataaatgt gtgaagttgg    8160
agtataccct taccttctta tttggctttg tgatagttta atttatatgt attttgagtt    8220
ctgacttgta tttctttgaa ttgattctag tttaagtaat ccatggccca cagcaagcac    8280
ggcctgaagg aggagatgac catgaagtac cacatggagg gctgcgtgaa cggccacaag    8340
ttcgtgatca ccggcgaggg catcggctac cccttcaagg gcaagcagac catcaacctg    8400
tgcgtgatcg agggcggccc cctgcccttc agcgaggaca tcctgagcgc cggcttcaag    8460
tacggcgacc ggatcttcac cgagtacccc caggacatcg tggactactt caagaacagc    8520
tgcccccgcg gctacacctg ggccggagc ttcctgttcg aggacggcgc cgtgtgcatc     8580
tgtaacgtgg acatcaccgt gagcgtgaag gagaactgca tctaccacaa gagcatcttc    8640
aacggcgtga acttccccgc cgacggcccc gtgatgaaga gatgaccac caactgggag     8700 gccagctgcg agaagatcat gcccgtgcct aagcagggca tcctgaaggg cgacgtgagc    8760
atgtacctgc tgctgaagga cggcggccgg taccggtgcc agttcgacac cgtgtacaag    8820
gccaagagcg tgcccagcaa gatgcccgag tggcacttca tccagcacaa gctgctgcgg    8880
gaggaccgga cgacgccaa gaaccagaag tggcagctga ccgagcacgc catcgccttc     8940
cccagcgccc tggcctgaga gctcgaattt ccccgatcgt tcaaacattt ggcaataaag    9000
tttcttaaga ttgaatcctg ttgccggtct tgcgatgatt atcatataat ttctgttgaa    9060
ttacgttaag catgtaataa ttaacatgta atgcatgacg ttatttatga gatgggtttt    9120
tatgattaga gtcccgcaat tatacattta atacgcgata gaaaacaaaa tatagcgcgc    9180
aaactaggat aaattatcgc gcgcggtgtc atctatgtta ctagatcggg aattctagtg    9240
gccggcccag ctgatatcca tcacactggc ggccgcactc gactgaattg gttccggcgc    9300
cagcctgctt t    9311

<210> SEQ ID NO 22
<211> LENGTH: 4842
<212> TYPE: DNA
<213> ORGANISM: artificial sequence
<220> FEATURE:
<223> OTHER INFORMATION: vector

<400> SEQUENCE: 22
cttgtacaaa gtggttgatg ggatccatgg cccacagcaa gcacggcctg aaggaggaga      60
tgaccatgaa gtaccacatg gagggctgcg tgaacggcca caagttcgtg atcaccggcg     120
agggcatcgg ctaccccttc aagggcaagc agaccatcaa cctgtgcgtg atcgagggcg     180
gccccctgcc cttcagcgag gacatcctga gcgccggctt caagtacggc gaccggatct     240
tcaccgagta ccccccaggac atcgtggact acttcaagaa cagctgcccc gccggctaca     300
cctggggccg gagcttcctg ttcgaggacg gcgccgtgtg catctgtaac gtggacatca     360
ccgtgagcgt gaaggagaac tgcatctacc acaagagcat cttcaacggc gtgaacttcc     420
ccgccgacgg ccccgtgatg aagaagatga ccaccaactg ggaggccagc tgcgagaaga     480
tcatgcccgt gcctaagcag ggcatcctga agggcgacgt gagcatgtac ctgctgctga     540
aggacggcgg ccggtaccgg tgccagttcg acaccgtgta caaggccaag agcgtgccca     600
gcaagatgcc cgagtggcac ttcatccagc acaagctgct gcgggaggac cggagcgacg     660
ccaagaacca gaagtggcag ctgaccgagc acgccatcgc cttccccagc gccctggcct     720
gagagctcga atttccccga tcgttcaaac atttggcaat aaagtttctt aagattgaat     780
cctgttgccg gtcttgcgat gattatcata taatttctgt tgaattacgt taagcatgta     840
```

-continued

| | |
|---|---|
| ataattaaca tgtaatgcat gacgttattt atgagatggg tttttatgat tagagtcccg | 900 |
| caattataca tttaatacgc gatagaaaac aaaatatagc gcgcaaacta ggataaatta | 960 |
| tcgcgcgcgg tgtcatctat gttactagat cgggaattct agtggccggc ccagctgata | 1020 |
| tccatcacac tggcggccgc tcgagttcta tagtgtcacc taaatcgtat gtgtatgata | 1080 |
| cataaggtta tgtattaatt gtagccgcgt tctaacgaca atatgtccat atggtgcact | 1140 |
| ctcagtacaa tctgctctga tgccgcatag ttaagccagc cccgacaccc gccaacaccc | 1200 |
| gctgacgcgc cctgacgggc ttgtctgctc ccggcatccg cttacagaca agctgtgacc | 1260 |
| gtctccggga gctgcatgtg tcagaggttt tcaccgtcat caccgaaacg cgcgagacga | 1320 |
| aagggcctcg tgatacgcct atttttatag gttaatgtca tgaccaaaat cccttaacgt | 1380 |
| gagttttcgt tccactgagc gtcagacccc gtagaaaaga tcaaaggatc ttcttgagat | 1440 |
| cctttttttc tgcgcgtaat ctgctgcttg caaacaaaaa aaccaccgct accagcggtg | 1500 |
| gtttgtttgc cggatcaaga gctaccaact cttttttccga aggtaactgg cttcagcaga | 1560 |
| gcgcagatac caaatactgt ccttctagtg tagccgtagt taggccacca cttcaagaac | 1620 |
| tctgtagcac cgcctacata cctcgctctg ctaatcctgt taccagtggc tgctgccagt | 1680 |
| ggcgataagt cgtgtcttac cgggttggac tcaagacgat agttaccgga taaggcgcag | 1740 |
| cggtcgggct gaacggggg ttcgtgcaca cagcccagct tggagcgaac gacctacacc | 1800 |
| gaactgagat acctacagcg tgagcattga aaagcgcca cgcttcccga agggagaaag | 1860 |
| gcggacaggt atccggtaag cggcagggtc ggaacaggag agcgcacgag ggagcttcca | 1920 |
| gggggaaacg cctggtatct ttatagtcct gtcgggtttc gccacctctg acttgagcgt | 1980 |
| cgattttgt gatgctcgtc agggggcgg agcctatgga aaaacgccag caacgcggcc | 2040 |
| ttttttacggt tcctggcctt ttgctggcct tttgctcaca tgttctttcc tgcgttatcc | 2100 |
| cctgattctg tggataaccg tattaccgcc tttgagtgag ctgataccgc tcgccgcagc | 2160 |
| cgaacgaccg agcgcagcga gtcagtgagc gaggaagcgg aagagcgccc aatacgcaaa | 2220 |
| ccgcctctcc ccgcgcgttg gccgattcat taatgcaggt tgatcagatc tcgatcccgc | 2280 |
| gaaattaata cgactcacta tagggagacc acaacggttt ccctctagaa ataattttgt | 2340 |
| ttaactttaa gaaggagata tacccatgga aaagcctgaa ctcaccgcga cgtctgtcga | 2400 |
| gaagtttctg atcgaaaagt tcgacagcgt ctccgacctg atgcagctct cggagggcga | 2460 |
| agaatctcgt gctttcagct tcgatgtagg agggcgtgga tatgtcctgc gggtaaatag | 2520 |
| ctgcgccgat ggtttctaca agatcgtta tgtttatcgg cactttgcat cggccgcgct | 2580 |
| cccgattccg gaagtgcttg acattgggga attcagcgag agcctgacct attgcatctc | 2640 |
| ccgccgtgca cagggtgtca cgttgcaaga cctgcctgaa accgaactgc ccgctgttct | 2700 |
| gcagccggtc gcggaggcta tggatgcgat cgctgcggcc gatcttagcc agacgagcgg | 2760 |
| gttcggccca ttcggaccgc aaggaatcgg tcaatacact acatggcgtg atttcatatg | 2820 |
| cgcgattgct gatccccatg tgtatcactg gcaaactgtg atggacgaca ccgtcagtgc | 2880 |
| gtccgtcgcg caggctctcg atgagctgat gctttgggcc gaggactgcc ccgaagtccg | 2940 |
| gcacctcgtg cacgcggatt tcggctccaa caatgtcctg acggacaatg gccgcataac | 3000 |
| agcggtcatt gactggagcg aggcgatgtt cggggattcc caatacgagg tcgccaacat | 3060 |
| cttcttctgg aggccgtggt tggcttgtat ggagcagcag acgcgctact cgagcggag | 3120 |
| gcatccggag cttgcaggat cgccgcggct ccgggcgtat atgctccgca ttggtcttga | 3180 |
| ccaactctat cagagcttgg ttgacggcaa tttcgatgat gcagcttggg cgcagggtcg | 3240 |

-continued

```
atgcgacgca atcgtccgat ccggagccgg gactgtcggg cgtacacaaa tcgcccgcag    3300
aagcgcggcc gtctggaccg atggctgtgt agaagtactc gccgatagtg aaaccgacg     3360 ccccagcact cgtccgaggg caaaggaata gtgaggtaca gcttggatcg atccggctgc    3420
taacaaagcc cgaaaggaag ctgagttggc tgctgccacc gctgagcaat aactagcata    3480
accccttggg gcctctaaac gggtcttgag gggtttttg ctgaaaggag gaactatatc     3540
cggatgatcg tcgaggcctc acgtgttaac aagcttgcat gcctgcaggt ttatcaacaa    3600
gtttgtacaa aaaagcaggc tccgaattcg cccttatagg aatagtttta ctattcactg    3660
ctttaataga aaatagttt aaattaaag atagtttaa tcccagcatt tgccacgttt       3720
gaacgtgagc cgaaacgatg tcgttacatt atcttaacct agctgaaacg atgtcgtcat    3780
aatatcgcca aatgccaact ggactacgtc gaacccacaa atcccacaaa gcgcgtgaaa    3840
tcaaatcgct caaccacaa aaaagaacaa cgcgtttgtt acacgctcaa tcccacgcga     3900
gtagagcaca gtaaccttca aataagcgaa tggggcataa tcagaaatcc gaaataaacc    3960
taggggcatt atcggaaatg aaagtagct cactcaatat aaaaatctag gaaccctagt     4020
tttcgttatc actctgtgct ccctcgctct atttctcagt ctctgtgttt gcggctgagg    4080
attccgaacg agtgaccttc ttcgtttctc gcaaaggtaa cagcctctgc tcttgtctct    4140
tcgattcgat ctatgcctgt ctcttattta cgatgatgtt tcttcggtta tgttttttta   4200
tttatgcttt atgctgttga tgtcggttg tttgtttcgc tttgttttg tggttcagtt     4260 ttttaggatt cttttggttt ttgaatcgat taatcggaag agattttcga gttatttggt   4320
gtgttggagg tgaatctttt ttttgaggtc atagatctgt tgtatttgtg ttataaacat   4380
gcgactttgt atgatttttt acgaggttat gatgttctgg ttgttttatt atgaatctgt   4440
tgagacagaa ccatgatttt tgttgatgtt cgtttacact attaaaggtt tgttttaaca   4500
ggattaaaag ttttttaagc atgttgaagg agtcttgtag atatgtaacc gtcgatagtt   4560
tttttgtggg tttgttcaca tgttatcaag cttaatctt tactatgtat gcgaccatat    4620
ctggatccag caaaggcgat ttttaattc cttgtgaaac ttttgtaata tgaagttgaa    4680
attttgttat tggtaaacta taaatgtgtg aagttggagt ataccttac cttcttattt     4740 ggctttgtga tagtttaatt tatatgtatt ttgagttctg acttgtatt ctttgaattg     4800 attctagttt aagtaatcca agggcgaatt cgacccagct tt                       4842
```

<210> SEQ ID NO 23
<211> LENGTH: 17
<212> TYPE: DNA
<213> ORGANISM: artificial sequence
<220> FEATURE:
<223> OTHER INFORMATION: MPSS TAG sequence

<400> SEQUENCE: 23
gatcggcggt aacattt                                                    17

<210> SEQ ID NO 24
<211> LENGTH: 26
<212> TYPE: DNA
<213> ORGANISM: artificial sequence
<220> FEATURE:
<223> OTHER INFORMATION: primer

<400> SEQUENCE: 24
gaccaagaca cactcgttca tatatc                                          26

<210> SEQ ID NO 25

```
<211> LENGTH: 25
<212> TYPE: DNA
<213> ORGANISM: artificial sequence
<220> FEATURE:
<223> OTHER INFORMATION: primer

<400> SEQUENCE: 25
tctgctgctc aatgtttaca aggac                                           25

<210> SEQ ID NO 26
<211> LENGTH: 19
<212> TYPE: DNA
<213> ORGANISM: artificial sequence
<220> FEATURE:
<223> OTHER INFORMATION: primer

<400> SEQUENCE: 26
agtgtccgcc gatttcatg                                                  19

<210> SEQ ID NO 27
<211> LENGTH: 20
<212> TYPE: DNA
<213> ORGANISM: artificial sequence
<220> FEATURE:
<223> OTHER INFORMATION: primer

<400> SEQUENCE: 27
aacgaaaatg ttaccgccga                                                 20

<210> SEQ ID NO 28
<211> LENGTH: 24
<212> TYPE: DNA
<213> ORGANISM: artificial sequence
<220> FEATURE:
<223> OTHER INFORMATION: primer

<400> SEQUENCE: 28
catgattggg agaaacctta agct                                            24

<210> SEQ ID NO 29
<211> LENGTH: 20
<212> TYPE: DNA
<213> ORGANISM: artificial sequence
<220> FEATURE:
<223> OTHER INFORMATION: primer

<400> SEQUENCE: 29
agattgggcc agaggatcct                                                 20

<210> SEQ ID NO 30
<211> LENGTH: 25
<212> TYPE: DNA
<213> ORGANISM: artificial sequence
<220> FEATURE:
<223> OTHER INFORMATION: primer

<400> SEQUENCE: 30
actgggctga caactgaggt taagt                                           25

<210> SEQ ID NO 31
<211> LENGTH: 20
<212> TYPE: DNA
<213> ORGANISM: artificial sequence
<220> FEATURE:
<223> OTHER INFORMATION: primer

<400> SEQUENCE: 31
```

```
ctacatgaaa tcggcggaca                                                     20

<210> SEQ ID NO 32
<211> LENGTH: 25
<212> TYPE: DNA
<213> ORGANISM: artificial sequence
<220> FEATURE:
<223> OTHER INFORMATION: primer

<400> SEQUENCE: 32
gacaggcata gatcgaatcg aagag                                               25

<210> SEQ ID NO 33
<211> LENGTH: 22
<212> TYPE: DNA
<213> ORGANISM: artificial sequence
<220> FEATURE:
<223> OTHER INFORMATION: primer

<400> SEQUENCE: 33
ggaagaagag aatcgggtgg tt                                                  22

<210> SEQ ID NO 34
<211> LENGTH: 23
<212> TYPE: DNA
<213> ORGANISM: artificial sequence
<220> FEATURE:
<223> OTHER INFORMATION: probe

<400> SEQUENCE: 34
attgtgttgt gtggcatggt tat                                                 23

<210> SEQ ID NO 35
<211> LENGTH: 23
<212> TYPE: DNA
<213> ORGANISM: artificial sequence
<220> FEATURE:
<223> OTHER INFORMATION: primer

<400> SEQUENCE: 35
ggcttgttgt gcagtttttg aag                                                 23

<210> SEQ ID NO 36
<211> LENGTH: 20
<212> TYPE: DNA
<213> ORGANISM: artificial sequence
<220> FEATURE:
<223> OTHER INFORMATION: primer

<400> SEQUENCE: 36
aacggccaca agttcgtgat                                                     20

<210> SEQ ID NO 37
<211> LENGTH: 20
<212> TYPE: DNA
<213> ORGANISM: artificial sequence
<220> FEATURE:
<223> OTHER INFORMATION: probe

<400> SEQUENCE: 37
accggcgagg gcatcggcta                                                     20

<210> SEQ ID NO 38
<211> LENGTH: 20
<212> TYPE: DNA
<213> ORGANISM: artificial sequence
<220> FEATURE:
```

<223> OTHER INFORMATION: primer

<400> SEQUENCE: 38
cttcaagggc aagcagacca                                          20

<210> SEQ ID NO 39
<211> LENGTH: 24
<212> TYPE: DNA
<213> ORGANISM: artificial sequence
<220> FEATURE:
<223> OTHER INFORMATION: primer

<400> SEQUENCE: 39
caaacttgac aaagccacaa ctct                                     24

<210> SEQ ID NO 40
<211> LENGTH: 20
<212> TYPE: DNA
<213> ORGANISM: artificial sequence
<220> FEATURE:
<223> OTHER INFORMATION: probe

<400> SEQUENCE: 40
ctctcatctc atataaatac                                          20

<210> SEQ ID NO 41
<211> LENGTH: 21
<212> TYPE: DNA
<213> ORGANISM: artificial sequence
<220> FEATURE:
<223> OTHER INFORMATION: primer

<400> SEQUENCE: 41
ggagaaattg gtgtcgtgga a                                        21

<210> SEQ ID NO 42
<211> LENGTH: 100
<212> TYPE: DNA
<213> ORGANISM: artificial sequence
<220> FEATURE:
<223> OTHER INFORMATION: recombination site

<400> SEQUENCE: 42
caaataatga ttttattttg actgatagtg acctgttcgt tgcaacaaat tgataagcaa      60 tgcttttttta taatgccaac tttgtacaaa aaagcaggct                          100

<210> SEQ ID NO 43
<211> LENGTH: 100
<212> TYPE: DNA
<213> ORGANISM: artificial sequence
<220> FEATURE:
<223> OTHER INFORMATION: recombination site

<400> SEQUENCE: 43
caaataatga ttttattttg actgatagtg acctgttcgt tgcaacaaat tgataagcaa      60 tgctttcttta taatgccaac tttgtacaag aaagctgggt                          100

<210> SEQ ID NO 44
<211> LENGTH: 125
<212> TYPE: DNA
<213> ORGANISM: artificial sequence
<220> FEATURE:
<223> OTHER INFORMATION: recombination site

<400> SEQUENCE: 44

```
acaagtttgt acaaaaaagc tgaacgagaa acgtaaaatg atataaatat caatatatta      60
aattagattt tgcataaaaa acagactaca taatactgta aaacacaaca tatccagtca     120
ctatg                                                                 125
```

<210> SEQ ID NO 45
<211> LENGTH: 125
<212> TYPE: DNA
<213> ORGANISM: artificial sequence
<220> FEATURE:
<223> OTHER INFORMATION: recombination site

<400> SEQUENCE: 45

```
accactttgt acaagaaagc tgaacgagaa acgtaaaatg atataaatat caatatatta      60
aattagattt tgcataaaaa acagactaca taatactgta aaacacaaca tatccagtca     120
ctatg                                                                 125
```

<210> SEQ ID NO 46
<211> LENGTH: 21
<212> TYPE: DNA
<213> ORGANISM: artificial sequence
<220> FEATURE:
<223> OTHER INFORMATION: recombination site

<400> SEQUENCE: 46

```
caagtttgta caaaaaagca g                                                21
```

<210> SEQ ID NO 47
<211> LENGTH: 21
<212> TYPE: DNA
<213> ORGANISM: artificial sequence
<220> FEATURE:
<223> OTHER INFORMATION: recombination site

<400> SEQUENCE: 47

```
cagctttctt gtacaaagtg g                                                21
```

<210> SEQ ID NO 48
<211> LENGTH: 8409
<212> TYPE: DNA
<213> ORGANISM: artificial sequence
<220> FEATURE:
<223> OTHER INFORMATION: vector

<400> SEQUENCE: 48

```
atcaaccact ttgtacaaga aagctgaacg agaaacgtaa aatgatataa atatcaatat      60
attaaattag attttgcata aaaaacagac tacataatac tgtaaaacac aacatatcca     120
gtcactatgg tcgacctgca gactggctgt gtataaggga gcctgacatt tatattcccc     180
agaacatcag gttaatggcg tttttgatgt cattttcgcg gtggctgaga tcagccactt     240
cttccccgat aacggagacc ggcacactgg ccatatcggt ggtcatcatg cgccagcttt     300
catccccgat atgcaccacc gggtaaagtt cacgggagac tttatctgac agcagacgtg     360
cactggccag ggggatcacc atccgtcgcc cgggcgtgtc aataatatca ctctgtacat     420
ccacaaacag acgataacgg ctctctcttt tataggtgta aaccttaaac tgcatttcac     480
cagcccctgt tctcgtcagc aaaagagccg ttcatttcaa taaaccgggc gacctcagcc     540
atcccttcct gattttccgc tttccagcgt tcggcacgca gacgacgggc ttcattctgc     600
atggttgtgc ttaccagacc ggagatattg acatcatata tgccttgagc aactgatagc     660
tgtcgctgtc aactgtcact gtaatacgct gcttcatagc atacctcttt ttgacatact     720
```

```
tcgggtatac atatcagtat atattcttat accgcaaaaa tcagcgcgca aatacgcata    780
ctgttatctg gcttttagta agccggatcc agatctttac gccccgccct gccactcatc    840
gcagtactgt tgtaattcat taagcattct gccgacatgg aagccatcac aaacggcatg    900
atgaacctga atcgccagcg gcatcagcac cttgtcgcct tgcgtataat atttgcccat    960
ggtgaaaacg ggggcgaaga agttgtccat attggccacg tttaaatcaa actggtgaa   1020 actcacccag ggattggctg agacgaaaaa catattctca ataaacccctt tagggaaata  1080 ggccaggttt tcaccgtaac acgccacatc ttgcgaatat atgtgtagaa actgccggaa   1140
atcgtcgtgg tattcactcc agagcgatga aaacgtttca gtttgctcat ggaaaacggt   1200
gtaacaaggg tgaacactat cccatatcac cagctcaccg tctttcattg ccatacggaa   1260
ttccggatga gcattcatca ggcgggcaag aatgtgaata aaggccggat aaaacttgtg   1320
cttatttttc tttacggtct ttaaaaaggc cgtaatatcc agctgaacgg tctggttata   1380
ggtacattga gcaactgact gaaatgcctc aaaatgttct ttacgatgcc attgggatat   1440
atcaacggtg gtatatccag tgattttttt ctccatttta gcttccttag ctcctgaaaa   1500
tctcgacgga tcctaactca aaatccacac attatacgag ccggaagcat aaagtgtaaa   1560
gcctggggtg cctaatgcgg ccgccaatat gactggatat gttgtgtttt acagtattat   1620
gtagtctgtt ttttatgcaa aatctaattt aatatattga tatttatatc attttacgtt   1680
tctcgttcag ctttttttgta caaacttgtt gatggggtta acatatcata acttcgtata   1740
atgtatgcta tacgaagtta taggcctgga tcttcgaggt cgagcggccg cagatttagg   1800
tgacactata gaatatgcat cactagtaag ctttgctcta gatcaaactc acatccaaac   1860
ataacatgga tatcttcctt accaatcata ctaattattt tgggttaaat attaatcatt   1920 attttttaaga tattaattaa gaaattaaaa gatttttttaa aaaaatgtat aaaattatat   1980
tattcatgat ttttcataca tttgattttg ataataaata tattttttttt aatttcttaa   2040 aaaatgttgc aagacactta ttagacatag tcttgttctg tttacaaaag cattcatcat   2100
ttaatacatt aaaaaatatt taatactaac agtagaatct tcttgtgagt ggtgtgggag   2160
taggcaacct ggcattgaaa cgagagaaag agagtcagaa ccagaagaca aataaaaagt   2220
atgcaacaaa caaatcaaaa tcaaagggca aaggctgggg ttggctcaat tggttgctac   2280
attcaatttt caactcagtc aacggttgag attcactctg acttccccaa tctaagccgc   2340
ggatgcaaac ggttgaatct aacccacaat ccaatctcgt tacttagggg cttttccgtc   2400
attaactcac ccctgccacc cggtttccct ataaattgga actcaatgct cccctctaaa   2460
ctcgtatcgc ttcagagttg agaccaagac acactcgttc atatatctct ctgctcttct   2520
cttctcttct acctctcaag gtacttttct tctccctcta ccaaatccta gattccgtgg   2580
ttcaatttcg gatcttgcac ttctggtttg ctttgccttg cttttttcctc aactgggtcc   2640 atctaggatc catgtgaaac tctactcttt ctttaatatc tgcggaatac gcgtttgact   2700
ttcagatcta gtcgaaatca tttcataatt gcctttcttt cttttagctt atgagaaata   2760
aaatcacttt ttttttattt caaaataaac cttgggcctt gtgctgactg agatggggtt   2820
tggtgattac agaattttag cgaattttgt aattgtactt gtttgtctgt agttttgttt   2880
tgttttcttg tttctcatac attccttagg cttcaatttt attcgagtat aggtcacaat   2940
aggaattcaa actttgagca ggggaattaa tcccttcctt caaatccagt tgtttgtat    3000 atatgtttaa aaaatgaaac ttttgcttta aattctatta taactttttt tatggctgaa   3060 attttttgcat gtgtctttgc tctctgttgt aaatttactg tttaggtact aactctaggc   3120
```

```
ttgttgtgca gttttttgaag tataaccatg ccacacaaca caatggcggc caccgcttcc    3180
agaaccaccc gattctcttc ttcctcttca cacccccacct tccccaaacg cattactaga   3240
tccaccctcc ctctctctca tcaaaccctc accaaaccca accacgctct caaaatcaaa   3300
tgttccatct ccaaacccc cacgcggcg cccttcacca aggaagcgcc gaccacggag      3360
cccttcgtgt cacggttcgc ctccggcgaa cctcgcaagg gcgcggacat ccttgtggag   3420
gcgctggaga ggcagggcgt gacgacggtg ttcgcgtacc ccggcggtgc gtcgatggag   3480
atccaccagg cgctcacgcg ctccgccgcc atccgcaacg tgctcccgcg ccacgagcag   3540
ggcggcgtct tcgccgccga aggctacgcg cgttcctccg gcctcccgg cgtctgcatt    3600 gccacctccg gccccggcgc caccaacctc gtgagcggcc tcgccgacgc tttaatggac   3660
agcgtcccag tcgtcgccat caccggccag gtcgcccgcc ggatgatcgg caccgacgcc   3720
ttccaagaaa ccccgatcgt ggaggtgagc agatccatca cgaagcacaa ctacctcatc   3780
ctcgacgtcg acgacatccc ccgcgtcgtc gccgaggctt tcttcgtcgc cacctccggc   3840
cgccccggtc cggtcctcat cgacattccc aaagacgttc agcagcaact cgccgtgcct   3900
aattgggacg agcccgttaa cctccccggt tacctcgcca ggctgcccag gccccccgcc   3960
gaggcccaat tggaacacat tgtcagactc atcatggagg cccaaaagcc cgttctctac   4020
gtcggcggtg gcagtttgaa ttccagtgct gaattgaggc gctttgttga actcactggt   4080
attcccgttg ctagcacttt aatgggtctt ggaactttc ctattggtga tgaatattcc    4140
cttcagatgc tgggtatgca tggtactgtt tatgctaact atgctgttga caatagtgat   4200
ttgttgcttg cctttggggt aaggtttgat gaccgtgtta ctgggaagct tgaggctttt   4260
gctagtaggg ctaagattgt tcacattgat attgattctg ccgagattgg gaagaacaag   4320
caggcgcacg tgtcggtttg cgcggatttg aagttggcct tgaagggaat taatatgatt   4380
ttggaggaga aaggagtgga gggtaagttt gatcttggag gttggagaga agagattaat   4440
gtgcagaaac acaagtttcc attgggttac aagacattcc aggacgcgat ttctccgcag   4500
catgctatcg aggttcttga tgagttgact aatggagatg ctattgttag tactgggtt    4560 gggcagcatc aaatgtgggc tgcgcagttt tacaagtaca agagaccgag gcagtggttg   4620
acctcagggg gtcttggagc catgggtttt ggattgcctg cggctattgg tgctgctgtt   4680
gctaaccctg gggctgttgt ggttgacatt gatgggatg gtagtttcat catgaatgtt   4740
caggagttgg ccactataag agtggagaat ctcccagtta agatattgtt gttgaacaat   4800
cagcatttgg gtatggtggt tcagttggag gataggttct acaagtccaa tagagctcac   4860
acctatcttg gagatccgtc tagcgagagc gagatattcc caaacatgct caagtttgct   4920
gatgcttgtg ggataccggc agcgcgagtg acgaagaagg aagagcttag gcggcaatt    4980 cagagaatgt tggacacccc tggccccctac cttcttgatg tcattgtgcc ccatcaggag   5040
catgtgttgc cgatgattcc cagtaatgga tccttcaagg atgtgataac tgagggtgat   5100
ggtagaacga ggtactgatt gcctagacca aatgttcctt gatgcttgtt ttgtacaata   5160 tataaagat aatgctgtcc tagttgcagg atttggcctg tggtgagcat catagtctgt    5220
agtagttttg gtagcaagac attttatttt cctttatttt aacttactac atgcagtagc   5280
atctatctat ctctgtagtc tgatatctcc tgttgtctgt attgtgccgt tggattttt    5340 gctgtagtga gactgaaaat gatgtgctag taataatatt tctgttagaa atctaagtag   5400
agaatctgtt gaagaagtca aaagctaatg gaatcaggtt acatattcaa tgttttttctt  5460 tttttagcgg ttggtagacg tgtagattca acttctcttg gagctcacct aggcaatcag   5520
```

```
taaaatgcat attccttttt taacttgcca tttatttact tttagtggaa attgtgacca   5580
atttgttcat gtagaacgga tttggaccat tgcgtccaca aaacgtctct tttgctcgat   5640
cttcacaaag cgataccgaa atccagagat agttttcaaa agtcagaaat ggcaaagtta   5700
taaatagtaa aacagaatag atgctgtaat cgacttcaat aacaagtggc atcacgtttc   5760
tagttctaga cccatcagat cgaattaaca tatcataact tcgtataatg tatgctatac   5820
gaagttatag gcctggatcc actagttcta gagcggccgc tcgagggggg gcccggtacc   5880
ggcgcgccgt tctatagtgt cacctaaatc gtatgtgtat gatacataag gttatgtatt   5940
aattgtagcc gcgttctaac gacaatatgt ccatatggtg cactctcagt acaatctgct   6000
ctgatgccgc atagttaagc cagccccgac acccgccaac acccgctgac gcgccctgac   6060
gggcttgtct gctcccggca tccgcttaca gacaagctgt gaccgtctcc gggagctgca   6120
tgtgtcagag gttttcaccg tcatcaccga aacgcgcgag acgaaagggc ctcgtgatac   6180
gcctattttt ataggttaat gtcatgacca aaatccctta acgtgagttt tcgttccact   6240
gagcgtcaga ccccgtagaa aagatcaaag gatcttcttg agatcctttt tttctgcgcg   6300
taatctgctg cttgcaaaca aaaaaaccac cgctaccagc ggtggtttgt ttgccggatc   6360
aagagctacc aactcttttt ccgaaggtaa ctggcttcag cagagcgcag ataccaaata   6420
ctgtccttct agtgtagccg tagttaggcc accacttcaa gaactctgta gcaccgccta   6480
catacctcgc tctgctaatc ctgttaccag tggctgctgc cagtggcgat aagtcgtgtc   6540
ttaccgggtt ggactcaaga cgatagttac cggataaggc gcagcggtcg ggctgaacgg   6600
ggggttcgtg cacacagccc agcttggagc gaacgaccta caccgaactg agatacctac   6660
agcgtgagca ttgagaaagc gccacgcttc ccgaagggag aaaggcggac aggtatccgg   6720
taagcggcag ggtcggaaca ggagagcgca cgagggagct tccaggggga aacgcctggt   6780
atctttatag tcctgtcggg tttcgccacc tctgacttga gcgtcgattt ttgtgatgct   6840
cgtcaggggg gcggagccta tggaaaaacg ccagcaacgc ggccttttta cggttcctgg   6900
ccttttgctg gccttttgct cacatgttct ttcctgcgtt atcccctgat tctgtggata   6960
accgtattac cgcctttgag tgagctgata ccgctcgccg cagccgaacg accgagcgca   7020
gcgagtcagt gagcgaggaa gcggaagagc gcccaatacg caaaccgcct ctccccgcgc   7080
gttggccgat tcattaatgc aggttgatca gatctcgatc ccgcgaaatt aatacgactc   7140
actataggga gaccacaacg gtttccctct agaaataatt ttgtttaact ttaagaagga   7200
gatatacccca tggaaaagcc tgaactcacc gcgacgtctg tcgagaagtt tctgatcgaa   7260
aagttcgaca gcgtctccga cctgatgcag ctctcggagg gcgaagaatc tcgtgctttc   7320
agcttcgatg taggagggcg tggatatgtc ctgcgggtaa atagctgcgc cgatggtttc   7380
tacaaagatc gttatgttta tcggcacttt gcatcggccg cgctcccgat tccggaagtg   7440
cttgacattg gggaattcag cgagagcctg acctattgca tctcccgccg tgcacagggt   7500
gtcacgttgc aagacctgcc tgaaaccgaa ctgcccgctg ttctgcagcc ggtcgcggag   7560
gctatggatg cgatcgctgc ggccgatctt agccagacga gcgggttcgg cccattcgga   7620
ccgcaaggaa tcggtcaata cactacatgg cgtgatttca tatgcgcgat tgctgatccc   7680
catgtgtatc actggcaaac tgtgatggac gacaccgtca gtgcgtccgt cgcgcaggct   7740
ctcgatgagc tgatgctttg ggccgaggac tgccccgaag tccggcacct cgtgcacgcg   7800
gatttcggct ccaacaatgt cctgacggac aatggccgca taacagcggt cattgactgg   7860
agcgaggcga tgttcgggga ttcccaatac gaggtcgcca acatcttctt ctggaggccg   7920
```

```
tggttggctt gtatggagca gcagacgcgc tacttcgagc ggaggcatcc ggagcttgca    7980
ggatcgccgc ggctccgggc gtatatgctc cgcattggtc ttgaccaact ctatcagagc    8040
ttggttgacg gcaatttcga tgatgcagct tgggcgcagg gtcgatgcga cgcaatcgtc    8100
cgatccggag ccgggactgt cgggcgtaca caaatcgccc gcagaagcgc ggccgtctgg    8160
accgatggct gtgtagaagt actcgccgat agtggaaacc gacgcccag  cactcgtccg    8220 agggcaaagg aatagtgagg tacagcttgg atcgatccgg ctgctaacaa agcccgaaag    8280
gaagctgagt tggctgctgc caccgctgag caataactag cataacccct tggggcctct    8340
aaacgggtct tgaggggttt tttgctgaaa ggaggaacta tatccggatg atcgggcgcg    8400
ccggtaccc                                                             8409

<210> SEQ ID NO 49
<211> LENGTH: 5286
<212> TYPE: DNA
<213> ORGANISM: artificial sequence
<220> FEATURE:
<223> OTHER INFORMATION: vector

<400> SEQUENCE: 49
atcaacaagt ttgtacaaaa aagctgaacg agaaacgtaa aatgatataa atatcaatat      60
attaaattag attttgcata aaaaacagac tacataatac tgtaaaacac aacatatcca     120
gtcatattgg cggccgcatt aggcacccca ggctttacac tttatgcttc cggctcgtat     180
aatgtgtgga ttttgagtta ggatccgtcg agattttcag gagctaagga agctaaaatg     240
gagaaaaaaa tcactggata taccaccgtt gatatatccc aatggcatcg taaagaacat     300
tttgaggcat ttcagtcagt tgctcaatgt acctataacc agaccgttca gctggatatt     360
acggcctttt taaagaccgt aaagaaaaat aagcacaagt tttatccggc ctttattcac     420
attcttgccc gcctgatgaa tgctcatccg gaattccgta tggcaatgaa agacggtgag     480
ctggtgatat gggatagtgt tcacccttgt tacaccgttt tccatgagca aactgaaacg     540
ttttcatcgc tctggagtga ataccacgac gatttccggc agtttctaca catatattcg     600
caagatgtgg cgtgttacgg tgaaaacctg gcctatttcc ctaaagggtt tattgagaat     660 atgttttcg  tctcagccaa tccctgggtg agtttcacca gttttgattt aaacgtggcc     720
aatatggaca cttcttcgc  ccccgttttc accatgggca atatattac  gcaaggcgac     780 aaggtgctga tgccgctggc gattcaggtt catcatgccg tttgtgatgg cttccatgtc     840
ggcagaatgc ttaatgaatt acaacagtac tgcgatgagt ggcagggcgg ggcgtaaaga     900
tctggatccg gcttactaaa agccagataa cagtatgcgt atttgcgcgc tgatttttgc     960
ggtataagaa tatatactga tatgtatacc cgaagtatgt caaaaagagg tatgctatga    1020
agcagcgtat tacagtgaca gttgacagcg acagctatca gttgctcaag gcatatatga    1080
tgtcaatatc tccggtctgg taagcacaac catgcagaat gaagcccgtc gtctgcgtgc    1140
cgaacgctgg aaagcggaaa atcaggaagg gatggctgag gtcgcccggt ttattgaaat    1200
gaacggctct tttgctgacg agaacagggg ctggtgaaat gcagtttaag gtttacacct    1260
ataaaagaga gagccgttat cgtctgtttg tggatgtaca gagtgatatt attgacacgc    1320
ccgggcgacg gatggtgatc ccctggcca  gtgcacgtct gctgtcagat aaagtctccc    1380
gtgaacttta cccggtggtg catatcgggg atgaaagctg gcgcatgatg accaccgata    1440
tggccagtgt gccggtctcc gttatcgggg aagaagtggc tgatctcagc caccgcgaaa    1500
atgacatcaa aaacgccatt aacctgatgt tctggggaat aaatgtcag  ggctccctta    1560
```

```
tacacagcca gtctgcaggt cgaccatagt gactggatat gttgtgtttt acagtattat    1620
gtagtctgtt tttatgcaa aatctaattt aatatattga tatttatatc attttacgtt    1680
tctcgttcag ctttcttgta caaagtggtt gatgggatcc atgcccaca gcaagcacgg    1740
cctgaaggag gagatgacca tgaagtacca catggagggc tgcgtgaacg ccacaagtt    1800
cgtgatcacc ggcgagggca tcggctaccc cttcaagggc aagcagacca tcaacctgtg    1860
cgtgatcgag ggcggccccc tgcccttcag cgaggacatc ctgagcgccg gcttcaagta    1920
cggcgaccgg atcttcaccg agtaccccca ggacatcgtg gactacttca gaacagctg    1980
ccccgccggc tacacctggg gccggagctt cctgttcgag gacggcgccg tgtgcatctg    2040
taacgtggac atcaccgtga gcgtgaagga gaactgcatc taccacaaga gcatcttcaa    2100
cggcgtgaac ttccccgccg acggccccgt gatgaagaag atgaccacca actgggaggc    2160
cagctgcgag aagatcatgc ccgtgcctaa gcagggcatc ctgaagggcg acgtgagcat    2220
gtacctgctg ctgaaggacg gcggccgta ccggtgccag ttcgacaccg tgtacaaggc    2280
caagagcgtg cccagcaaga tgcccgagtg gcacttcatc cagcacaagc tgctgcggga    2340
ggaccggagc gacgccaaga accagaagtg gcagctgacc gagcacgcca tcgccttccc    2400
cagcgccctg gcctgagagc tcgaatttcc ccgatcgttc aaacatttgg caataaagtt    2460
tcttaagatt gaatcctgtt gccggtcttg cgatgattat catataattt ctgttgaatt    2520
acgttaagca tgtaataatt aacatgtaat gcatgacgtt atttatgaga tgggttttta    2580
tgattagagt cccgcaatta tacatttaat acgcgataga aaacaaaata tagcgcgcaa    2640
actaggataa attatcgcgc gcggtgtcat ctatgttact agatcgggaa ttctagtggc    2700
cggcccagct gatatccatc acactggcgg ccgctcgagt tctatagtgt cacctaaatc    2760
gtatgtgtat gatacataag gttatgtatt aattgtagcc gcgttctaac gacaatatgt    2820
ccatatggtg cactctcagt acaatctgct ctgatgccgc atagttaagc cagccccgac    2880
acccgccaac acccgctgac gcgccctgac gggcttgtct gctcccggca tccgcttaca    2940
gacaagctgt gaccgtctcc gggagctgca tgtgtcagag gttttcaccg tcatcaccga    3000
aacgcgcgag acgaaagggc ctcgtgatac gcctattttt ataggttaat gtcatgacca    3060
aaatccctta acgtgagttt tcgttccact gagcgtcaga ccccgtagaa aagatcaaag    3120
gatcttcttg agatcctttt tttctgcgcg taatctgctg cttgcaaaca aaaaaaccac    3180
cgctaccagc ggtggtttgt ttgccggatc aagagctacc aactcttttt ccgaaggtaa    3240
ctggcttcag cagagcgcag ataccaaata ctgtccttct agtgtagccg tagttaggcc    3300
accacttcaa gaactctgta gcaccgccta catacctcgc tctgctaatc ctgttaccag    3360
tggctgctgc cagtggcgat aagtcgtgtc ttaccgggtt ggactcaaga cgatagttac    3420
cggataaggc gcagcggtcg ggctgaacgg ggggttcgtg cacacagccc agcttggagc    3480
gaacgaccta caccgaactg agatacctac agcgtgagca ttgagaaagc gccacgcttc    3540
ccgaagggag aaaggcggac aggtatccgg taagcggcag ggtcggaaca ggagagcgca    3600
cgagggagct tccagggga aacgcctggt atctttatag tcctgtcggg tttcgccacc    3660
tctgacttga gcgtcgattt ttgtgatgct cgtcaggggg gcggagccta tggaaaaacg    3720
ccagcaacgc ggcctttta cggttcctgg cttttgctg ccttttgct cacatgttct    3780
ttcctgcgtt atcccctgat tctgtggata accgtattac cgcctttgag tgagctgata    3840
ccgctcgccg cagccgaacg accgagcgca gcgagtcagt gagcgaggaa gcggaagagc    3900
gcccaatacg caaaccgcct ctccccgcgc gttggccgat tcattaatgc aggttgatca    3960
```

```
gatctcgatc ccgcgaaatt aatacgactc actatagggga gaccacaacg gtttccctct    4020
agaaataatt ttgtttaact ttaagaagga gatatacccca tggaaaagcc tgaactcacc    4080
gcgacgtctg tcgagaagtt tctgatcgaa aagttcgaca gcgtctccga cctgatgcag    4140
ctctcggagg gcgaagaatc tcgtgctttc agcttcgatg taggagggcg tggatatgtc    4200
ctgcgggtaa atagctgcgc cgatggtttc tacaaagatc gttatgttta tcggcacttt    4260
gcatcggccg cgctcccgat tccggaagtg cttgacattg gggaattcag cgagagcctg    4320
acctattgca tctcccgccg tgcacagggt gtcacgttgc aagacctgcc tgaaaccgaa    4380
ctgcccgctg ttctgcagcc ggtcgcggag gctatggatg cgatcgctgc ggccgatctt    4440
agccagacga gcgggttcgg cccattcgga ccgcaaggaa tcggtcaata cactacatgg    4500
cgtgatttca tatgcgcgat tgctgatccc catgtgtatc actggcaaac tgtgatggac    4560
gacaccgtca gtgcgtccgt cgcgcaggct ctcgatgagc tgatgctttg ggccgaggac    4620
tgccccgaag tccggcacct cgtgcacgcg gatttcggct ccaacaatgt cctgacggac    4680
aatggccgca taacagcggt cattgactgg agcgaggcga tgttcgggga ttcccaatac    4740
gaggtcgcca acatcttctt ctggaggccg tggttggctt gtatggagca gcagacgcgc    4800
tacttcgagc ggaggcatcc ggagcttgca ggatcgccgc ggctccgggc gtatatgctc    4860
cgcattggtc ttgaccaact ctatcagagc ttggttgacg gcaatttcga tgatgcagct    4920
tgggcgcagg gtcgatgcga cgcaatcgtc cgatccggag ccgggactgt cgggcgtaca    4980
caaatcgccc gcagaagcgc ggccgtctgg accgatggct gtgtagaagt actcgccgat    5040
agtggaaacc gacgcccccag cactcgtccg agggcaaagg aatagtgagg tacagcttgg    5100
atcgatccgg ctgctaacaa agcccgaaag gaagctgagt tggctgctgc caccgctgag    5160
caataactag cataaccccct tggggcctct aaacgggtct tgagggggttt tttgctgaaa    5220 ggaggaacta tatccggatg atcgtcgagg cctcacgtgt taacaagctt gcatgcctgc    5280
aggttt                                                               5286
```

SOYBEAN EF1A2 PROMOTER AND ITS USE IN CONSTITUTIVE EXPRESSION OF TRANSGENIC GENES IN PLANTS

This application claims priority to U.S. Provisional Application No. 60/989,172, filed Nov. 20, 2007, the entire contents of which are hereby incorporated by reference in their entirety.

FIELD OF THE INVENTION

This invention relates to a plant promoter GM-EF1A2 and fragments thereof and their use in altering expression of at least one heterologous nucleic acid fragment in plants in a tissue-independent or constitutive manner.

BACKGROUND

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities, can be incorporated properly into the plant's genome. The newly integrated gene (or genes) coding sequence can then be expressed in the plant cell to exhibit the desired new trait or characteristics. It is important that appropriate regulatory signals must be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the enzyme and other related protein factors that attach to it and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cell to cause termination of the RNA synthesis and the addition of polyadenylate nucleotides to the 3' end.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since the patterns of the expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

Certain promoters are able to direct RNA synthesis at relatively similar levels across all tissues of a plant. These are called "constitutive promoters" or "tissue-independent" promoters. Constitutive promoters can be divided into strong, moderate and weak according to their effectiveness to direct RNA synthesis. Since it is necessary in many cases to simultaneously express a chimeric gene (or genes) in different tissues of a plant to get the desired functions of the gene (or genes), constitutive promoters are especially useful in this consideration. Though many constitutive promoters have been discovered from plants and plant viruses and characterized, there is still an ongoing interest in the isolation of more novel constitutive promoters which are capable of controlling the expression of a chimeric gene or (genes) at different levels and the expression of multiple genes in the same transgenic plant for gene stacking.

SUMMARY OF THE INVENTION

This invention concerns an isolated nucleic acid fragment comprising a promoter wherein said promoter consists essentially of the nucleotide sequence set forth in SEQ ID NOs: 1, 2, 3, 4, 5, 6, 7 or said promoter consists essentially of a fragment that is substantially similar and functionally equivalent to the nucleotide sequence set forth in SEQ ID NOs: 1, 2, 3, 4, 5, 6, 7.

In a second embodiment, this invention concerns a recombinant expression construct comprising at least one heterologous nucleic acid fragment operably linked to the promoter of the invention.

In a third embodiment, this invention concerns a cell, plant, or seed comprising a recombinant expression construct of the present disclosure.

In a fourth embodiment, this invention concerns plants comprising this recombinant expression construct and seeds obtained from such plants.

In a fifth embodiment, this invention concerns a method of altering (increasing or decreasing) expression of at least one heterologous nucleic acid fragment in a plant cell which comprises:
 (a) transforming a plant cell with the recombinant expression construct described above;
 (b) growing fertile mature plants from the transformed plant cell of step (a);
 (c) selecting plants containing the transformed plant cell wherein the expression of the heterologous nucleic acid fragment is increased or decreased.

In a sixth embodiment, this invention concerns a method for expressing a yellow fluorescent protein ZS-YELLOW1 N1 in a host cell comprising:
 (a) transforming a host cell with a recombinant expression construct comprising at least one ZS-YELLOW1 N1 (YFP) nucleic acid fragment operably linked to a promoter wherein said promoter consists essentially of the nucleotide sequence set forth in SEQ ID NOs:1, 2, 3, 4, 5, 6, or 7; and
 (b) growing the transformed host cell under conditions that are suitable for expression of the recombinant DNA construct, wherein expression of the recombinant DNA construct results in production of increased levels of ZS-YELLOW1 N1 protein in the transformed host cell when compared to a corresponding nontransformed host cell.

In a seventh embodiment, this invention concerns an isolated nucleic acid fragment comprising a plant translation elongation factor EF1A2 gene promoter.

In an eighth embodiment, this invention concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In a ninth embodiment, this invention concerns an isolated polynucleotide linked to a heterologous nucleic acid sequence. The heterologous nucleic acid sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

BRIEF DESCRIPTION OF THE DRAWINGS AND SEQUENCES

The invention can be more fully understood from the following detailed descriptions, the drawings and the sequence descriptions that form a part of this application. The sequence descriptions and sequence listing attached hereto comply with the rules governing nucleotide and/or amino acid sequence disclosures in patent applications as set forth in 37 C.F.R. §1.821-1.825. The sequence descriptions contain the three letter codes for amino acids as defined in 37 C.F.R. §1.821-1.825, which are incorporated herein by reference.

SEQ ID NO:1 is the DNA sequence comprising a 1502 bp (base pair) soybean EF1A2 promoter.

SEQ ID NO:2 is a 1184 bp truncated form of the EF1A2 promoter shown in SEQ ID NO:1 (bp 323-1502 of SEQ ID NO:1).

SEQ ID NO:3 is a 924 bp truncated form of the EF1A2 promoter shown in SEQ ID NO:1 (bp 583-1502 of SEQ ID NO:1).

SEQ ID NO:4 is a 682 bp truncated form of the EF1A2 promoter shown in SEQ ID NO:1 (bp 825-1502 of SEQ ID NO:1).

SEQ ID NO:5 is a 477 bp truncated form of the EF1A2 promoter shown in SEQ ID NO:1 (bp 1030-1502 of SEQ ID NO:1).

SEQ ID NO:6 is a 253 bp truncated form of the EF1A2 promoter shown in SEQ ID NO:1 (bp 1255-1054 of SEQ ID NO:1).

SEQ ID NO:7 is an oligonucleotide primer used as a sense primer in the PCR amplification of the full length EF1A2 promoter in SEQ ID NO:1 when paired with SEQ ID NO:8. A restriction enzyme XmaI recognition site CCCGGG is added for subsequent cloning.

SEQ ID NO:8 is an oligonucleotide primer used as an antisense primer in the PCR amplification of the full length EF1A2 promoter in SEQ ID NO:1 when paired with SEQ ID NO:7. A restriction enzyme NcoI recognition site CCATGG is added for subsequent cloning.

SEQ ID NO:9 is an oligonucleotide primer used as an antisense primer in the PCR amplifications of the truncated EF1A2 promoters in SEQ ID NOs:2, 3, 4, 5, or 6 when paired with SEQ ID NOs:10, 11, 12, 13, or 14, respectively.

SEQ ID NO:10 is an oligonucleotide primer used as a sense primer in the PCR amplification of the truncated EF1A2 promoter in SEQ ID NO:2 when paired with SEQ ID NO:9.

SEQ ID NO:11 is an oligonucleotide primer used as a sense primer in the PCR amplification of the truncated EF1A2 promoter in SEQ ID NO:3 when paired with SEQ ID NO:9.

SEQ ID NO:12 is an oligonucleotide primer used as a sense primer in the PCR amplification of the truncated EF1A2 promoter in SEQ ID NO:4 when paired with SEQ ID NO:9.

SEQ ID NO:13 is an oligonucleotide primer used as a sense primer in the PCR amplification of the truncated EF1A2 promoter in SEQ ID NO:5 when paired with SEQ ID NO:9.

SEQ ID NO:14 is an oligonucleotide primer used as a sense primer in the PCR amplification of the truncated EF1A2 promoter in SEQ ID NO:6 when paired with SEQ ID NO:9.

SEQ ID NO:15 is a 691 bp intron located in the 5' untranslated region (5UTR) of the EF1A2 gene as revealed by sequence alignment between the EF1A2 promoter and EF1A2 cDNA sequence.

SEQ ID NO:16 is a 75 bp putative 5' untranslated region (5UTR) upstream of the 691 bp intron SEQ ID NO:15 of the EF1A2 gene.

SEQ ID NO:17 is a 12 bp putative 5' untranslated region (5UTR) downstream of the 691 bp intron SEQ ID NO:15 of the EF1A2 gene. The last base pairs C is not naturally present in the EF1A2 gene and is introduced as a part of the NcoI cloning site CCATGG.

SEQ ID NO:18 is the 1778 bp nucleotide sequence of the putative soybean translation elongation factor EF1A2 gene. Nucleotides 1 to 92 are the 5' untranslated sequence, nucleotides 93 to 95 are the translation initiation codon, nucleotides 93 to 1433 are the polypeptide coding region, nucleotides 1434 to 1436 are the termination codon, and nucleotides 1437 to 1778 are part of the 3' untranslated sequence.

SEQ ID NO:19 is the predicted 447 aa (amino acid) long protein sequence translated from the coding region of the putative soybean translation elongation factor EF1A2 gene nucleotide sequence SEQ ID NO:18.

SEQ ID NO:20 is the 4786 bp sequence of QC363.

SEQ ID NO:21 is the 9311 bp sequence of QC364.

SEQ ID NO:22 is the 4842 bp sequence of QC363-1Y.

SEQ ID NO:23 is the 17 base signature tag used in the MPSS analysis described in Example 1.

SEQ ID NO:24 is an oligonucleotide primer used in the diagnostic PCR to check for soybean genomic DNA presence in total RNA or cDNA when paired with SEQ ID NO:24.

SEQ ID NO:25 is an oligonucleotide primer used in the diagnostic PCR to check for soybean genomic DNA presence in total RNA or cDNA when paired with SEQ ID NO:24.

SEQ ID NO:26 is a sense primer used in quantitative RT-PCR analysis of PSO333268 gene expression.

SEQ ID NO:27 is an antisense primer used in quantitative RT-PCR analysis of PSO333268 gene expression.

SEQ ID NO:28 is a sense primer used as an endogenous control gene primer in quantitative RT-PCR analysis of gene expression.

SEQ ID NO:29 is an antisense primer used as an endogenous control gene primer in quantitative RT-PCR analysis of gene expression.

SEQ ID NO:30 is a PSO333268 gene-specific sense primer used together with SEQ ID NO:31 to screen BAC (bacterial artificial chromosome) libraries to identify corresponding BAC clones.

SEQ ID NO:31 is a PSO333268 gene-specific antisense primer used together with SEQ ID NO:30 to screen BAC libraries to identify corresponding BAC clones.

SEQ ID NO:32 is a PSO333268 gene-specific antisense primer used together with SEQ ID NO:10 to make the EF1A2 probe for Southern hybridization.

SEQ ID NO:33 is a sense primer used in quantitative PCR analysis of SAMS:ALS transgene copy numbers.

SEQ ID NO:34 is a FAM labeled fluorescent DNA oligo probe used in quantitative PCR analysis of SAMS:ALS transgene copy numbers.

SEQ ID NO:35 is an antisense primer used in quantitative PCR analysis of SAMS:ALS transgene copy numbers.

SEQ ID NO:36 is a sense primer used in quantitative PCR analysis of GM-EF1A2:YFP transgene copy numbers.

SEQ ID NO:37 is a FAM labeled fluorescent DNA oligo probe used in quantitative PCR analysis of GM-EF1A2:YFP transgene copy numbers.

SEQ ID NO:38 is an antisense primer used in quantitative PCR analysis of GM-EF1A2:YFP transgene copy numbers.

SEQ ID NO:39 is a sense primer used as an endogenous control gene primer in quantitative PCR analysis of transgene copy numbers.

SEQ ID NO:40 is a VIC labeled DNA oligo probe used as an endogenous control gene probe in quantitative PCR analysis of transgene copy numbers.

SEQ ID NO:41 is an antisense primer used as an endogenous control gene primer in quantitative PCR analysis of transgene copy numbers.

SEQ ID NO:42 is the recombination site attL1 sequence in the Gateway cloning system (Invitrogen).

SEQ ID NO:43 is the recombination site attL2 sequence in the Gateway cloning system (Invitrogen).

SEQ ID NO:44 is the recombination site attR1 sequence in the Gateway cloning system (Invitrogen).

SEQ ID NO:45 is the recombination site attR2 sequence in the Gateway cloning system (Invitrogen).

SEQ ID NO:46 is the recombination site attB1 sequence in the Gateway cloning system (Invitrogen).

SEQ ID NO:47 is the recombination site attB2 sequence in the Gateway cloning system (Invitrogen).

SEQ ID NO:48 is the 8409 bp sequence of QC324i used as a destination vector in Gateway cloning.

SEQ ID NO:49 is the 5286 bp sequence of QC330 used as a destination vector in Gateway cloning.

Figure 5:
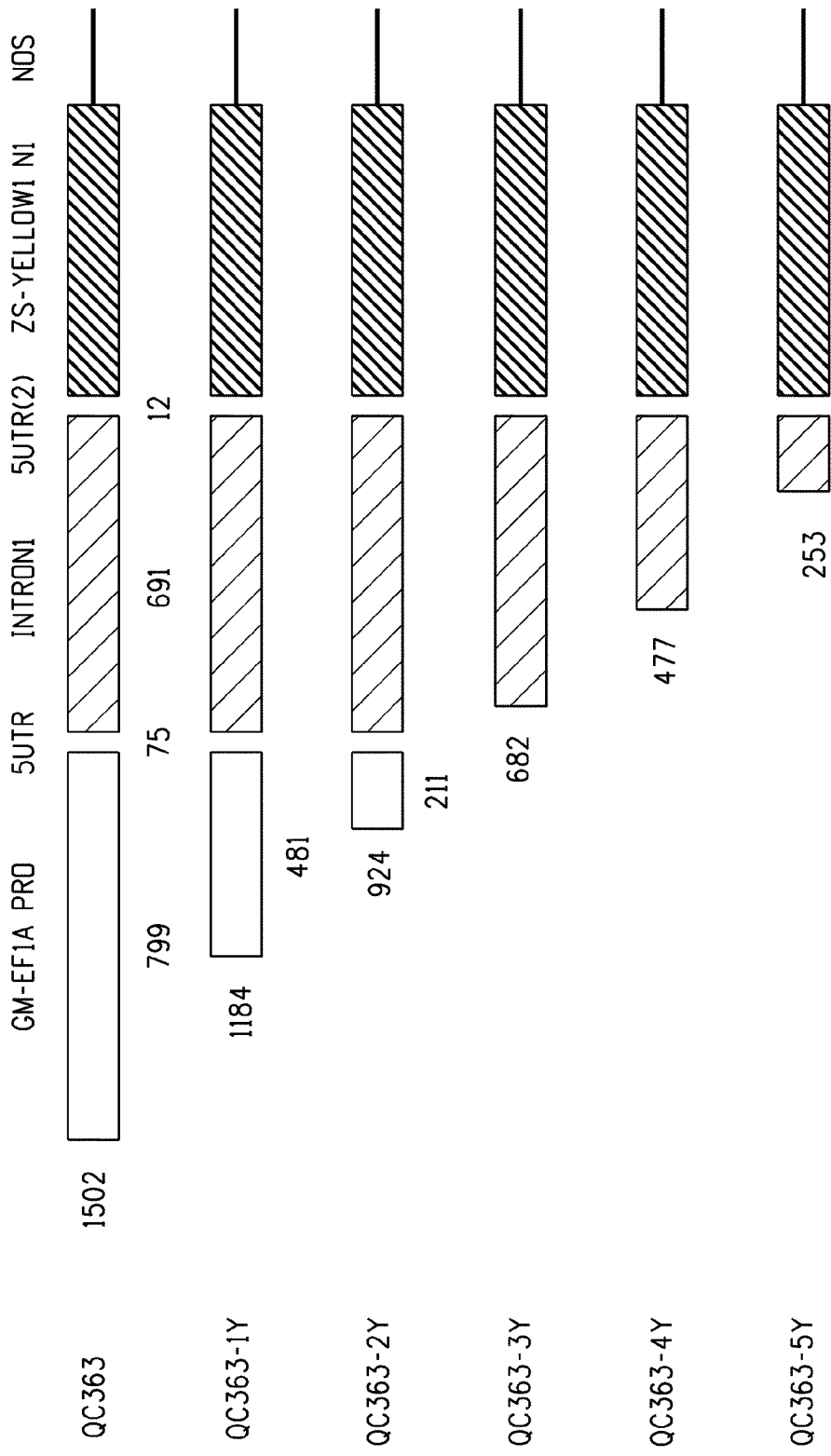

FIG. 5 is the schematic description of the full length construct QC363 and its progressive truncation constructs, QC363-1Y, QC363-2Y, QC363-3Y, QC363-4Y, and QC363-5Y, of the EF1A2 promoter. The size of each promoter deletion including the 5'UTR, 5'UTR intron, and 5'UTR (2) is given at the left end of each drawing. The size of the promoter region upstream of the 5'UTR is given under each drawing. The sizes of the 5'UTR, 5'UTR intron, and 5'UTR (2) are given under the QC363 drawing.

FIG. 6 is the transient expression of the fluorescent protein reporter gene ZS-YELLOW1 N1 in the cotyledons of germinating soybean seeds. The reporter gene is driven by the full length EF1A2 promoter in QC363 or by progressively truncated EF1A2 promoters in the transient expression constructs QC363-1Y to QC363-5Y.

FIG. 7 is the stable expression of the fluorescent protein reporter gene ZS-YELLOW1 N1 in transgenic soybean plants containing a single copy of the transgene construct QC364.

DETAILED DESCRIPTION OF THE INVENTION

The disclosure of all patents, patent applications, and publications cited herein are incorporated by reference in their entirety.

In the context of this disclosure, a number of terms shall be utilized.

As used herein, a "GM-EF1A2 promoter" refers to a promoter of the *Glycine max* EF-1-alpha polypeptide which is a putative soybean protein with significant homology to translation elongation factor EF-1α genes identified in various species including soybean (Aguilar et al, Plant Mol. Biol. 17 (3), 351-360 (1991)).

The term "constitutive promoter" refers to promoters active in all or most tissues of a plant at all or most developing stages. As with other promoters classified as "constitutive" (e.g. ubiquitin), some variation in absolute levels of expression can exist among different tissues or stages.

The term "constitutive promoter" or "tissue-independent" are used interchangeably herewithin.

The promoter nucleotide sequences and methods disclosed herein are useful in regulating constitutive expression of any heterologous nucleotide sequences in a host plant in order to alter the phenotype of a plant.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorosulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paroromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, Arabidopsis, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993); Roberts et al. Curr Opin Cell Biol 5, 242-246 (1993); Roberts et al. Annu Rev Plant Mol Biol 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al. BMC Bioinformatics 6:169 (2005)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Downregulation of the expression of the enzymes involved in raffinose saccharide synthesis, such as galactinol synthase for example, would be a desirable trait.

In certain embodiments, the present invention contemplates the transformation of a recipient cell with more than one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode) or drought resistance, oil quantity and quality, or those increasing yield or nutritional quality may be employed as desired.

An "isolated nucleic acid fragment" refers to a polymer of ribonucleotides (RNA) or deoxyribonucleotides (DNA) that is single- or double-stranded, optionally containing synthetic, non-natural or altered nucleotide bases. An isolated nucleic acid fragment in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "heterologous nucleic acid fragment" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The isolated promoter sequence of the present invention can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present invention can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended at levels about $1/10,000$ transcripts to about $1/100,000$ transcripts to about $1/500,000$ transcripts. Conversely, a strong promoter drives expression of a coding sequence at high level, or at about $1/10$ transcripts to about $1/100$ transcripts to about $1/1,000$ transcripts.

Nucleic acid molecules that are fragments of the promoter of the present invention comprise at least 20, 50, 75, 100, 150, 200, 250, 300, 350, 400, 450, 500 nucleotides, or up to the number of nucleotides present in a full-length nucleotide sequence disclosed herein (for example 1502, SEQ ID NO:1).

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2× SSC, 0.5% SDS was increased to 60° C. Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 80% to 100%, such as 81%, 82%, 83%, 84%, 85%, 86%, 87%, 88%, 89%, 90%, 91%, 92%, 93%, 94%, 95%, 96%, 97%, 98 and 99%.

A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent similarity calculations may be determined using the Megalign program of the LASARGENE bioinformatics computing suite (DNASTAR Inc., Madison, Wis.) or using the AlignX program of the Vector NTI bioinformatics computing suite (Invitrogen, Carlsbad, Calif.). Multiple alignment of the sequences are performed using the Clustal method of alignment (Higgins and Sharp, CABIOS 5:151-153 (1989)) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity. An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

Among the most commonly used promoters are the nopaline synthase (NOS) promoter (Ebert et al., Proc. Natl. Acad. Sci. U.S.A. 84:5745-5749 (1987)), the octapine synthase (OCS) promoter, caulimovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol.

14:433-43 (1990)), the light inducible promoter from the small subunit of rubisco, the Adh promoter (Walker et al., Proc. Natl. Acad. Sci. U.S.A. 84:6624-66280 (1987), the sucrose synthase promoter (Yang et al., Proc. Natl. Acad. Sci. U.S.A. 87:4144-4148 (1990)), the R gene complex promoter (Chandler et al., Plant Cell 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., Cell 29:1015-1026 (1982)). A plethora of promoters is described in PCT Publication No. WO 00/18963 published on Apr. 6, 2000, the disclosure of which is hereby incorporated by reference.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107, 065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product e.g., a mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at posttranscriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999; and PCT Publication No. WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083 published on Aug. 20, 1998). Genetic and molecular evidences have been obtained suggesting that dsRNA mediated mRNA cleavage may have been the conserved mechanism underlying these gene silencing phenomena (Elmayan et al., Plant Cell 10:1747-1757 (1998); Galun, In Vitro Cell. Dev. Biol. Plant 41 (2):113-123 (2005); Pickford et al, Cell. Mol. Life Sci. 60(5):871-882 (2003)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of soybean cell transformation is the use of particle-accelerated or "gene gun" transformation technology (Klein, T., Nature (London) 327:70-73 (1987); U.S. Pat. No. 4,945,050).

"Transient expression" refers to the temporary expression of often reporter genes such as β-glucuronidase (GUS), fluorescent protein genes GFP, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

A "recombinant expression construct" is a plasmid vector or a fragment thereof comprising the instant soybean constitutive promoter. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

The translation elongation factor EF1 alpha belongs to the GTP-binding elongation factor family and promotes the GTP-dependent binding of aminoacyl-tRNA to the A-site of ribosomes during protein biosynthesis. EF1 alpha genes and in some cases their promoters have been isolated from different plants including soybean (Aguilar et al, Plant Mol. Biol. 17(3):351-360 (1991)), Arabidopsis (Axelos et al, Mol. Gen. Genetics. 219:106-112 (1989)), tobacco (Aida et al, Japan Agric. Res. Quarterly 39(4):269-274 (2005)), potato (Nakane et al, J. Gen. Plant Pathol. 69:378-384 (2003)), tomato (Shewmaker et al, Nucleic Acids Res. 18(14):4276 (1990)), lily (Wang et al, J. Biol. Chem 274(17):12001-12008 (1999)), carrot (Kawahara et al, Eur. J. Biochem. 209(1):157-162 (1992)), and other plant species. The reported EF1 alpha genes are abundant especially in fast growing plant tissues in most cases. In at least one case, the tobacco EF1 alpha gene promoter has been reported to be more efficiently to express a report transgene than the 35S promoter of cauliflower mosaic virus (Aida et al, Japan Agric. Res. Quarterly 39(4): 269-274 (2005)). It is demonstrated herein that the soybean EF1A2 gene promoter can, in fact, be used as a constitutive promoter to drive efficient expression of transgenes, and that such promoter can be isolated and used by one skilled in the art.

This invention concerns an isolated nucleic acid fragment comprising a constitutive elongation factor EF1alpha gene promoter EF1A2. This invention also concerns an isolated nucleic acid fragment comprising a promoter wherein said promoter consists essentially of the nucleotide sequence set forth in SEQ ID NO:1, or said promoter consists essentially of a fragment that is substantially similar and functionally equivalent to the nucleotide sequence set forth in SEQ ID NO:1. A nucleic acid fragment that is functionally equivalent to the instant EF1A2 promoter is any nucleic acid fragment that is capable of controlling the expression of a coding sequence or functional RNA in a similar manner to the EF1A2 promoter. The expression patterns of EF1A2 gene and its promoter are set forth in Examples 1, 2, 7, and 8.

The promoter activity of the soybean genomic DNA fragment SEQ ID NO:1 upstream of the EF1A2 protein coding sequence was assessed by linking the fragment to a yellow fluorescence reporter gene, ZS-YELLOW1 N1 (YFP) (Matz et al, Nat. Biotechnol. 17:969-973 (1999)), transforming the promoter:YFP expression cassette into soybean, and analyzing YFP expression in various cell types of the transgenic plants (see Example 7 and 8). YFP expression was detected in all parts of the transgenic plants though stronger expression was detected in fast growing tissues such as developing embryos and pods. These results indicated that the nucleic acid fragment contained a constitutive promoter.

It is clear from the disclosure set forth herein that one of ordinary skill in the art could perform the following procedure:

1) operably linking the nucleic acid fragment containing the EF1A2 promoter sequence to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric EF1A2 promoter:reporter gene expression cassette into an appropriate plant for expression of the promoter. There are a variety of appropriate plants which can be used as a host for transformation that are well known to those skilled in the art, including the dicots, Arabidopsis, tobacco, soybean, oilseed rape, peanut, sunflower, safflower, cotton, tomato, potato, cocoa and the monocots, corn, wheat, rice, barley and palm.

3) testing for expression of the EF1A2 promoter in various cell types of transgenic plant tissues, e.g., leaves, roots, flowers, seeds, transformed with the chimeric EF1A2 promoter: reporter gene expression cassette by assaying for expression of the reporter gene product.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention EF1A2 promoter or a fragment that is substantially similar and functionally equivalent to any portion of the nucleotide sequence set forth in SEQ ID NOs:1, 2, 3, 4, 5, 6, or 7 to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this invention concerns a recombinant DNA construct comprising at least one acetolactate synthase (ALS) nucleic acid fragment operably linked to EF1A2 promoter, or combination of promoter elements, of the present invention. The acetolactate synthase gene is involved in the biosynthesis of branched chain amino acids in plants and is the site of action of several herbicides including sulfonyl urea. Expression of a mutated acetolactate synthase gene encoding a protein that can no longer bind the herbicide will enable the transgenic plants to be resistant to the herbicide (U.S. Pat. No. 5,605,011, U.S. Pat. No. 5,378,824). The mutated acetolactate synthase gene is also widely used in plant transformation to select transgenic plants.

In another embodiment, this invention concerns host cells comprising either the recombinant DNA constructs of the invention as described herein or isolated polynucleotides of the invention as described herein. Examples of host cells which can be used to practice the invention include, but are not limited to, yeast, bacteria, and plants.

Plasmid vectors comprising the instant recombinant expression construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Bio/Technology 6:923 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; $2^{nd}$ ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: N.Y., 1998; Birren et al., In Genome Analysis: Analyzing DNA, 2; Cold Spring Harbor: N.Y., 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

The level of activity of the EF1A2 promoter is comparable to that of many known strong promoters, such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the Arabidopsis oleosin promoters (Plant et al., Plant Mol. Biol. 25:193-205 (1994); Li, Texas A&M University Ph.D. dissertation, pp. 107-128 (1997)), the Arabidopsis ubiquitin extension protein promoters (Callis et al., J. Biol. Chem. 265(21):12486-12493 (1990)), a tomato ubiquitin gene promoter (Rollfinke et al., Gene 211:267-276 (1998)), a soybean heat shock protein promoter, and a maize H3 histone gene promoter (Atanassova et al., Plant Mol. Biol. 37:275-285 (1998)). Universal expression of chimeric genes in most plant cells makes the EF1A2 promoter of the instant invention especially useful when constitutive expression of a target heterologous nucleic acid fragment is required.

Another general application of the EF1A2 promoter of the invention is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to the EF1A2 promoter of the present invention. (See U.S. Pat. No. 5,231,020, and PCT Publication No. WO 99/53050 published on Oct. 21, 1999, PCT Publication No. WO 02/00904 published on Jan. 3, 2002, and PCT Publication No. WO 98/36083 published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the EF1A2 promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:

(a) transforming a plant cell with the recombinant expression construct described herein;
(b) growing fertile mature plants from the transformed plant cell of step (a);
(c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

EXAMPLES

The present invention is further defined in the following Examples, in which parts and percentages are by weight and degrees are Celsius, unless otherwise stated. Sequences of promoters, cDNA, adaptors, and primers listed in this invention all are in the 5' to 3' orientation unless described otherwise. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; 2$^{nd}$ ed.; Cold Spring Harbor Laboratory Press: Cold Spring Harbor, N.Y., 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Soybean Constitutive Promoter Candidate Genes

Soybean expression sequence tags (EST) were generated by sequencing randomly selected clones from cDNA libraries constructed from different soybean tissues. Multiple EST sequences could often be found with different lengths representing the different regions of the same soybean gene. If more EST sequences representing the same gene are more frequently found from a tissue-specific cDNA library such as a flower library than from a leaf library, there is a possibility that the represented gene could be a flower preferred gene candidate. Likewise, if similar numbers of ESTs for the same gene were found in various libraries constructed from different tissues, the represented gene could be a constitutively expressed gene. Multiple EST sequences representing the same soybean gene could be compiled electronically based on their overlapping sequence homology into a unique full length sequence representing the gene. These assembled unique gene sequences were accumulatively collected in Pioneer Hi-Bred Int'l proprietary searchable databases. To identify strong constitutive promoter candidate genes, searches were performed to look for gene sequences that were found at similar frequencies in leaf, root, flower, embryos, pod, and also in other libraries. One unique gene PSO333268 was identified in the search to be a constitutive gene candidate. PSO333268 cDNA sequence (SEQ ID NO:18) as well as its putative translated protein sequence (SEQ ID NO:19) were used to search National Center for Biotechnology Information (NCBI) databases. Both PSO333268 nucleotide and amino acid sequences were found to have high homology to translation elongation factor EF1 alpha genes discovered in several plants including soybean (Aguilar et al, Plant Mol. Biol. 17(3):351-360 (1991)).

Due to the limited number of ESTs representing PSO333268 in the databases, it was necessary to apply an additional analysis to confirm its gene expression profile. A more sensitive gene expression profiling methodology MPSS (Mass Parallel Signature Sequence) transcript profiling technique (Brenner et al., Proc Natl Acad Sci USA 97:1665-70 (2000)) was used to confirm that PSO333268 is indeed constitutively expressed. The MPSS technology involves the generation of 17 base signature tags from mRNA samples that have been reverse transcribed from poly A+RNA isolated using standard molecular biology techniques (Sambrook et al., 1989). The tags are simultaneously sequenced and assigned to genes or ESTs. The abundance of these tags is given a number value that is normalized to parts per million (PPM) which then allows the tag expression, or tag abundance, to be compared across different tissues. Thus, the MPSS platform can be used to determine the expression pattern of a particular gene and its expression levels in different tissues. MPSS gene expression profiles generated from different soybean tissues over the time have been accumulatively collected in Pioneer Hi-Bred Int'l proprietary searchable databases. The PSO333268 cDNA sequence was first used to search the databases to identify a MPSS tag sequence (SEQ ID NO: 23) that was unique and identical to a 17 base pair region in the 3' end of the PSO333268 cDNA sequence. The tag sequence was then used to search the databases again to reveal its abundance in different tissues. As illustrated in Table 1, the PSO333268 gene was confirmed to be highly abundant in all tissues, a desired expression profile for its promoter to be used as a constitutive promoter with stronger expression in seed and pod.

TABLE 1

Lynx MPSS Expression Profiles of the PSO333268 Gene

| | |
|---|---|
| Target gene | PSO333268 |
| Tag sequence | SEQ ID NO: 40 |
| Flower | 2715 |
| Pod | 5848 |
| Flower bud | 1901 |

TABLE 1-continued

Lynx MPSS Expression Profiles of the PSO333268 Gene

| | |
|---|---|
| Lateral root | 2121 |
| Leaf | 4810 |
| Petiole | 3275 |
| Primary root | 3028 |
| Seed | 7171 |
| Stem | 2533 |

Example 2

Quantitative RT-PCR Profiles of EF1A2 Gene Expression in Soybean

Figure 1:
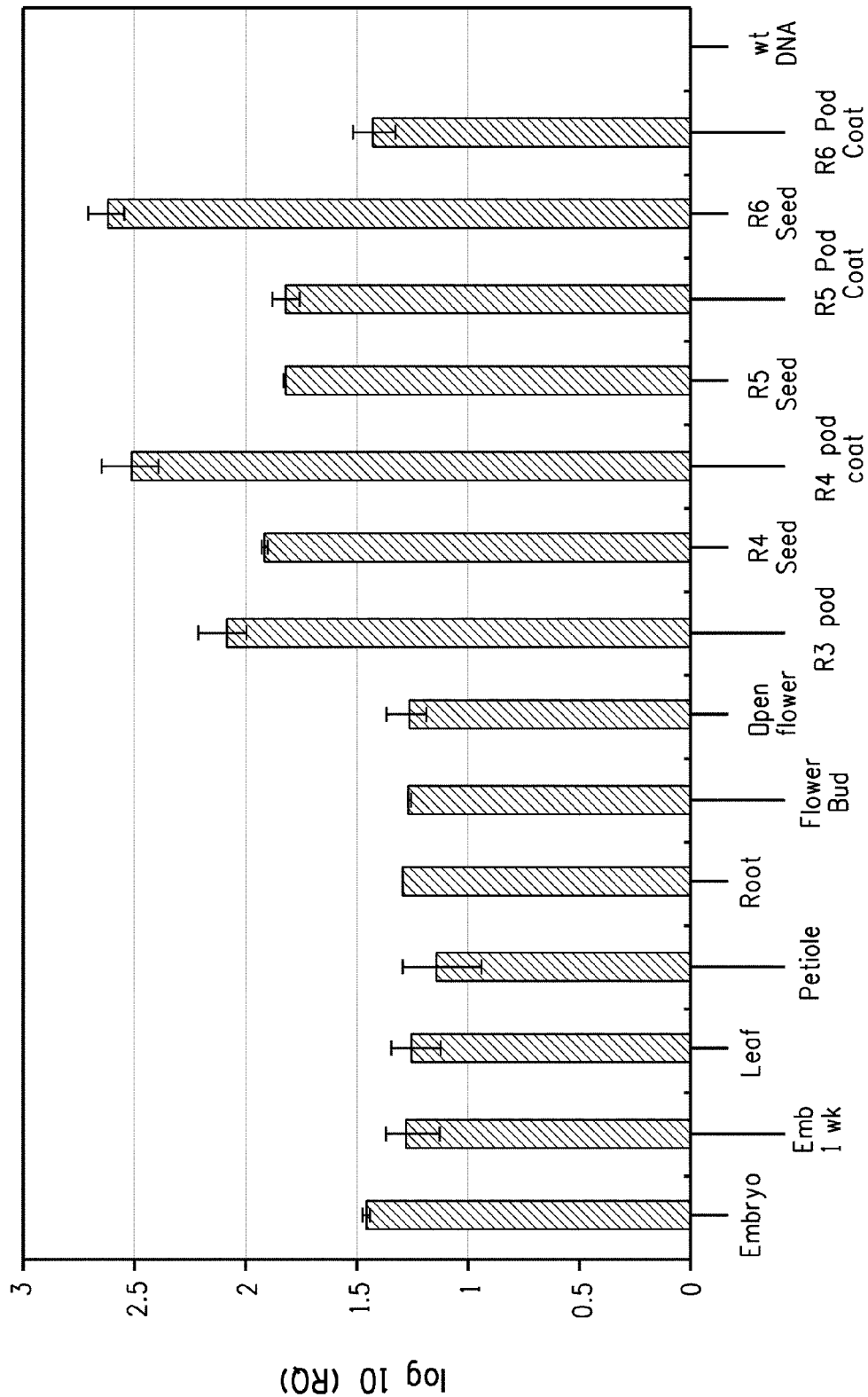
FIG. 1 is the logarithm of relative quantifications of the soybean EF1A2 gene expression in 14 different soybean tissues by quantitative RT-PCR. The gene expression profile indicates that the EF1A2 gene is highly expressed in all the checked tissues.

The MPSS profile of PSO333268 was confirmed and extended by analyzing 14 different soybean tissues using the relative quantitative RT-PCR technique with a ABI7500 real time PCR system (Applied Biosystems, Foster City, Calif.). Fourteen soybean tissues, somatic embryo, somatic embryo one week on charcoal plate, leaf, leaf petiole, root, flower bud, open flower, R3 pod, R4 seed, R4 pod coat, R5 seed, R5 pod coat, R6 seed, R6 pod coat were collected from cultivar 'Jack' and flash frozen in liquid nitrogen. The seed and pod development stages were defined according to descriptions in Fehr and Caviness, IWSRBC 80:1-12 (1977). Total RNA was extracted with Trizol reagents (Invitrogen, Carlsbad, Calif.) and treated with DNase I to remove any trace amount of genomic DNA contamination. The first strand cDNA was synthesized using the Superscript III reverse transcriptase (Invitrogen). Regular PCR analysis was done to confirm that the cDNA was free of any genomic DNA using primers shown in SEQ ID NO:24 and 25. The primers are specific to the 5'UTR intron/exon junction regions of a soybean S-adenosylmethionine synthetase gene promoter SAMS (Falco and Li, WO 00/37662 (2000)). PCR using this primer set will amplify a 967 bp DNA fragment from any soybean genomic DNA template and a 376 bp DNA fragment from the cDNA template. Genome DNA-free cDNA aliquots were used in quantitative RT-PCR analysis in which an endogenous soybean ATP sulfurylase gene was used as an internal control and wild type soybean genomic DNA was used as the calibrator for relative quantification. PSO33268 gene-specific primers SEQ ID NO:26 and 27 and ATPS gene-specific primers SEQ ID NO:28 and 29 were used in separate PCR reactions using the Power Sybr® Green real time PCR master mix (Applied Biosystems). PCR reaction data were captured and analyzed using the sequence detection software provided with the ABI7500 real time PCR system. The qRT-PCR profiling of the PSO333268 EF1A2 gene expression confirmed its strong and constitutive expression pattern (FIG. 1).

Example 3

Isolation of Soybean EF1A2 Promoter

A BAC clone sbach.pk123.f11 corresponding to PSO333268 was identified from the screening of Pioneer Hi-Bred Int'l propriety soybean BAC libraries using PSO333268 gene-specific primers SEQ ID NO:30 and 31 by PCR (polymerase chain reaction). The BAC clone was partially sequenced to reveal an approximately 2 Kb sequence upstream of PSO33268 EF1A2 gene coding region. The primers shown in SEQ ID NO:7 and 8 were then designed to amplify the putative full length 1502 bp EF1A2 promoter from the BAC clone DNA by PCR. SEQ ID NO:7 contains a recognition site for the restriction enzyme XmaI. SEQ ID NO:8 contains a recognition site for the restriction enzyme NcoI. In order to study promoter function, the EF1A2 promoter was cloned into an expression vector via the restriction enzymes sites.

PCR cycle conditions were 94° C. for 4 minutes; 35 cycles of 94° C. for 30 seconds, 60° C. for 1 minute, and 68° C. for 2 minutes; and a final 68° C. for 5 minutes before holding at 4° C. using the Platinum high fidelity Taq DNA polymerase (Invitrogen). The PCR reaction was resolved using agarose gel electrophoresis to identify the right size PCR product representing the ~1.5 Kb EF1A2 promoter. The PCR amplified DNA of the correct size was then digested with XmaI and NcoI restriction enzymes and the fragment was cloned into a Gateway (Invitrogen) cloning entry vector by conventional ligation to place the putative EF1A2 promoter upstream of the ZS-YELLOW N1 fluorescent reporter gene (YFP). Several clones containing the ~1.5 Kb DNA insert were sequenced and construct QC363 (FIG. 3, SEQ ID NO:20) was confirmed to contain the identical EF1A2 promoter sequence as previously sequenced from the BAC clone sbach.pk123.f11. The EF1A2 promoter sequence is herein listed as SEQ ID NO:1.

Sequence alignment analysis between the EF1A2 promoter sequence and the full length EF1 alpha cDNA sequence revealed that there is a 691 bp intron SEQ ID NO:15 in the 5'UTR (un-translated region). The promoter region upstream of the putative 5'UTR is 724 bp long. The 5'UTR is interrupted by the intron into a 75 bp fragment SEQ ID NO:16 upstream of the intron and a 12 bp fragment SEQ ID NO:17 downstream of the intron. The last base pair C in the 12 bp fragment is introduced as part of the cloning site NcoI CCATGG. The two 5'UTR fragments, the 5'UTR intron, and the upstream promoter region with a total of 1502 bp nucleotides (SEQ ID NO:1) are herein collectively called EF1A2 promoter.

Example 4

EF1A2 Promoter Copy Number Analysis

Figure 2A:
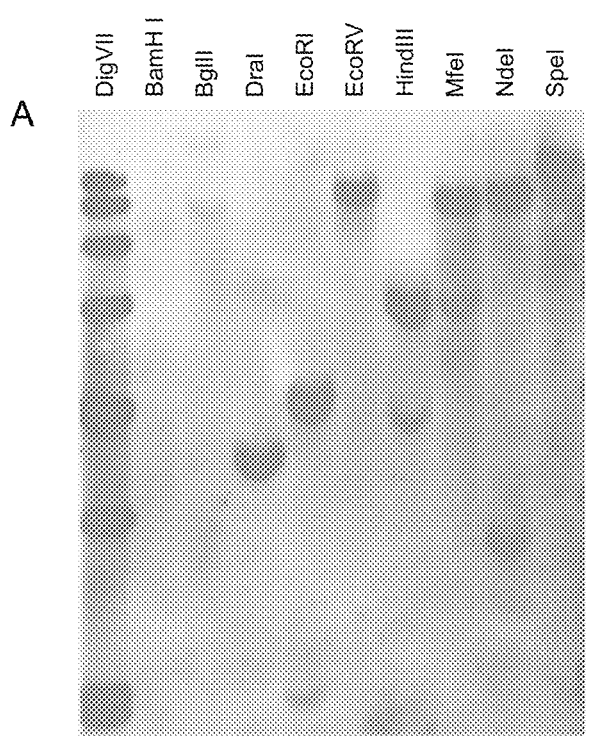
FIG. 2 is EF1A2 promoter copy number analysis by Southern.
Figure 2B:
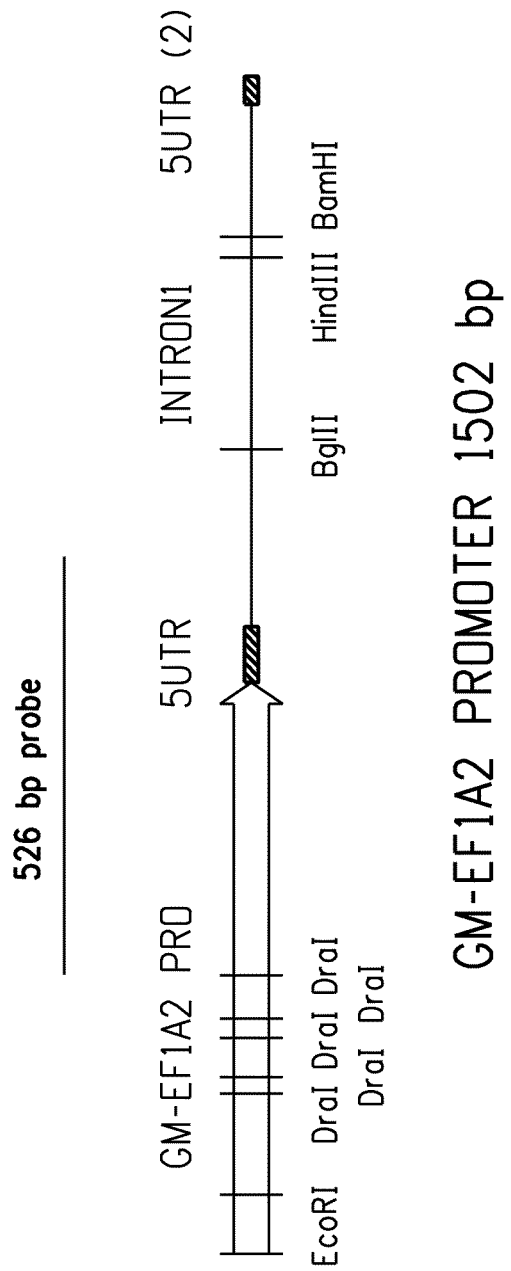

Southern hybridization analysis was performed to examine whether additional copies or sequences with significant similarity to the EF1A2 promoter exist in the soybean genome. Soybean 'Jack' wild type genomic DNA was digested with nine different restriction enzymes, BamHI, BglII, DraI, EcoRI, EcoRV, HindIII, MfeI, NdeI, and SpeI and distributed in a 0.7% agarose gel by electrophoresis. The DNA was blotted onto Nylon membrane and hybridized at 60° C. with digoxigenin labeled EF1A2 promoter DNA probe in Easy-Hyb Southern hybridization solution, and then sequentially washed 10 minutes with 2×SSC/0.1% SDS at room temperature and 3×10 minutes at 65° C. with 0.1×SSC/0.1% SDS according to the protocol provided by the manufacturer (Roche Applied Science, Indianapolis, Ind.). The EF1A2 promoter probe was labeled by PCR using the DIG DNA labeling kit (Roche Applied Science) with two gene specific primers SEQ ID NO:10 and SEQ ID NO:32 to make a 526 bp long probe corresponding to the middle region of the EF1A2 promoter (FIG. 2B).

According to the EF1A2 promoter sequence, only DraI would cut the 526 bp probe region but at the 5' end to produce a 54 bp fragment that would be too small to be retained on the Southern blot. None of the other eight restriction enzymes BamHI, BglII, EcoRI, EcoRV, HindII, MfeI, NdeI, and SpeI would cut the probe region. Therefore, only one band would be expected to hybridize to the probe for each of the nine different digestions if only one copy of EF1A2 sequence exists in the soybean genome (FIG. 2B). The observation that two bands were detected in five digestions including BgIII, EcoRI, HindII, MfeI, and NdeI suggested that there is another sequence in soybean genome with significant similarity to the EF1A2 promoter sequence SE ID NO:1 (FIG. 2A). The observation that no band was detected in the BamHI lane suggested that BamHI digestion did not produce an EF1A2 containing genomic DNA fragment of appropriate size that could be retained on the Southern blot.

Example 5

EF1A2:YFP Reporter Gene Constructs and Soybean Transformation

Figure 3A:
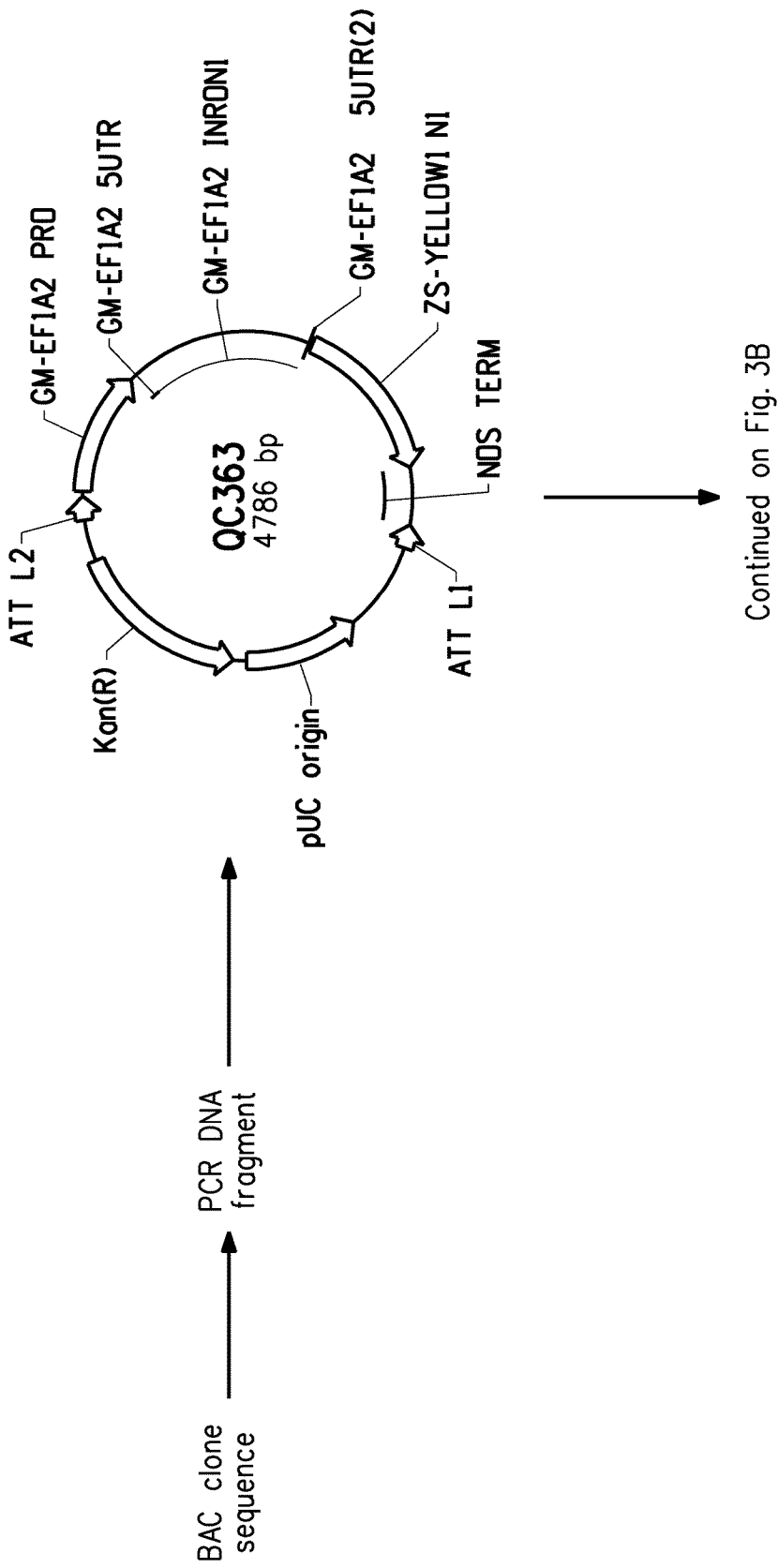
FIG. 3 shows the maps of plasmid QC363, QC324i, and QC364.

The EF1A2:YFP expression cassette in Gateway entry construct QC363 (SEQ ID NO:20) described in EXAMPLE 3 was moved into a Gateway destination vector QC324i (SEQ ID NO:48) by LR clonase mediated DNA recombination between the attL1 and attL2 recombination sites (SEQ ID NO:42, and 43, respectively) in QC363 and the attR1-attR2 recombination sites (SEQ ID NO:44, and 45, respectively) in QC324i (Invitrogen). Since the destination vector QC324i already contains a soybean transformation selectable marker gene SAMS:ALS, the resulting DNA construct QC364 (SEQ ID NO:21) has two gene expression cassettes EF1A2:YFP and SAMS:ALS linked together (FIG. 3). Two 21 bp recombination sites attB1 and attB2 (SEQ ID NO:46, and 47, respectively) were newly created recombination sites resulting from DNA recombination between attL1 and attR2, and between attL2 and attR2, respectively. The 6797 bp DNA fragment containing the linked EF1A:YFP and SAMS:ALS expression cassettes was isolated from plasmid QC364 (SEQ ID NO:21) with AscI digestion, separated from the vector backbone fragment by agarose gel electrophoresis, and purified from the gel with a DNA gel extraction kit (Qiagen, Valencia, Calif.). The purified DNA fragment was transformed to soybean cultivar Jack by the method of particle gun bombardment (Klein et al., Nature 327:70-73 (1987); U.S. Pat. No. 4,945,050) as described in detail below to study the EF1A2 promoter activity in stably transformed soybean plants.

The same methodology as outlined above for the EF1A:YFP expression cassette construction and transformation can be used with other heterologous nucleic acid sequences encoding for example a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

Soybean somatic embryos from the Jack cultivar were induced as follows. Cotyledons (~3 mm in length) were dissected from surface sterilized, immature seeds and were cultured for 6-10 weeks in the light at 26° C. on a Murashige and Skoog media containing 0.7% agar and supplemented with 10 mg/ml 2,4-D. Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 µl of a 60 mg/ml 1.0 mm gold particle suspension were added (in order): 30 µl of 30 ng/µl QC364 DNA fragment EF1A:YFP+SAMS:ALS, 20 µl of 0.1 M spermidine, and 25 µl of 5 M $CaCl_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. 5 µl of the DNA-coated gold particles was then loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production. Genomic DNA were extracted from somatic embryo samples and analyzed by quantitative PCR using the 7500 real time PCR system (Applied Biosystems) with gene-specific primers and FAM-labeled fluorescence probes to check copy numbers of both the SAMS:ALS expression cassette and the EF1A:YFP expression cassette. The qPCR analysis was done in duplex reactions with a heat shock protein (HSP) gene as the endogenous controls and a transgenic DNA sample with a known single copy of SAMS:ALS or YFP transgene as the calibrator using the relative quantification methodology (Applied Biosystems). The endogenous control HSP probe was labeled with VIC and the target gene SAMS or YFP probe was labeled with FAM for the simultaneous detection of both fluorescent probes (Applied Biosystems).

The primers and probes used in the qPCR analysis are listed below.

SAMS forward primer: SEQ ID NO:33
FAM labeled SAMS probe: SEQ ID NO:34
SAMS reverse primer: SEQ ID NO:35
YFP forward primer: SEQ ID NO:36
FAM labeled YFP probe: SEQ ID NO:37
YFP reverse primer: SEQ ID NO:38
HSP forward primer: SEQ ID NO:39
VIC labeled HSP probe: SEQ ID NO:40
HSP reverse primer: SEQ ID NO:41

Only transgenic soybean events containing 1 or 2 copies of both the SAMS:ALS expression cassette and the EF1A2:YFP expression cassette were selected for further gene expression evaluation and seed production (see Table 2). Events negative for YFP qPCR or with more than 2 copies for the SAMS qPCR were not further followed. YFP expressions are described in detail in EXAMPLE 8 and are also summarized in Table 2.

TABLE 2

Relative transgene copy numbers and YFP expression of EF1A2:YFP transgenic plants

| Event ID | YFP | YFP qPCR | SAMS qPCR |
| --- | --- | --- | --- |
| 5158.1.1 | + | 0.8 | 1.0 |
| 5158.1.2 | + | 1.0 | 1.4 |
| 5158.2.1 | + | 1.7 | 2.1 |
| 5158.4.1 | + | 0.7 | 0.9 |
| 5158.4.3 | + | 0.7 | 0.7 |
| 5158.7.1 | + | 0.9 | 0.7 |
| 5158.7.2 | + | 1.2 | 1.6 |
| 5158.4.5 | + | 1.5 | 1.6 |
| 5158.4.7 | + | 0.7 | 1.0 |
| 5158.4.8 | + | 1.4 | 1.1 |
| 5158.4.10 | + | 1.0 | 1.6 |
| 5158.4.12 | + | 0.8 | 1.0 |
| 5158.4.15 | + | 0.6 | 1.0 |
| 5158.7.4 | + | 0.8 | 0.8 |
| 5158.7.5 | + | 1.2 | 1.4 |
| 5158.7.6 | + | 0.8 | 0.8 |
| 5158.2.5 | + | 0.9 | 1.1 |
| 5158.4.16 | + | 0.4 | 1.1 |
| 5158.4.17 | + | 0.9 | 1.5 |
| 5158.4.26 | + | 1.6 | 1.6 |
| 5158.5.9 | + | 0.8 | 1.0 |
| 5158.5.11 | + | 0.8 | 0.9 |

Example 6

Construction of EF1A2 Promoter Deletion Constructs

Figures 4C, 4D:
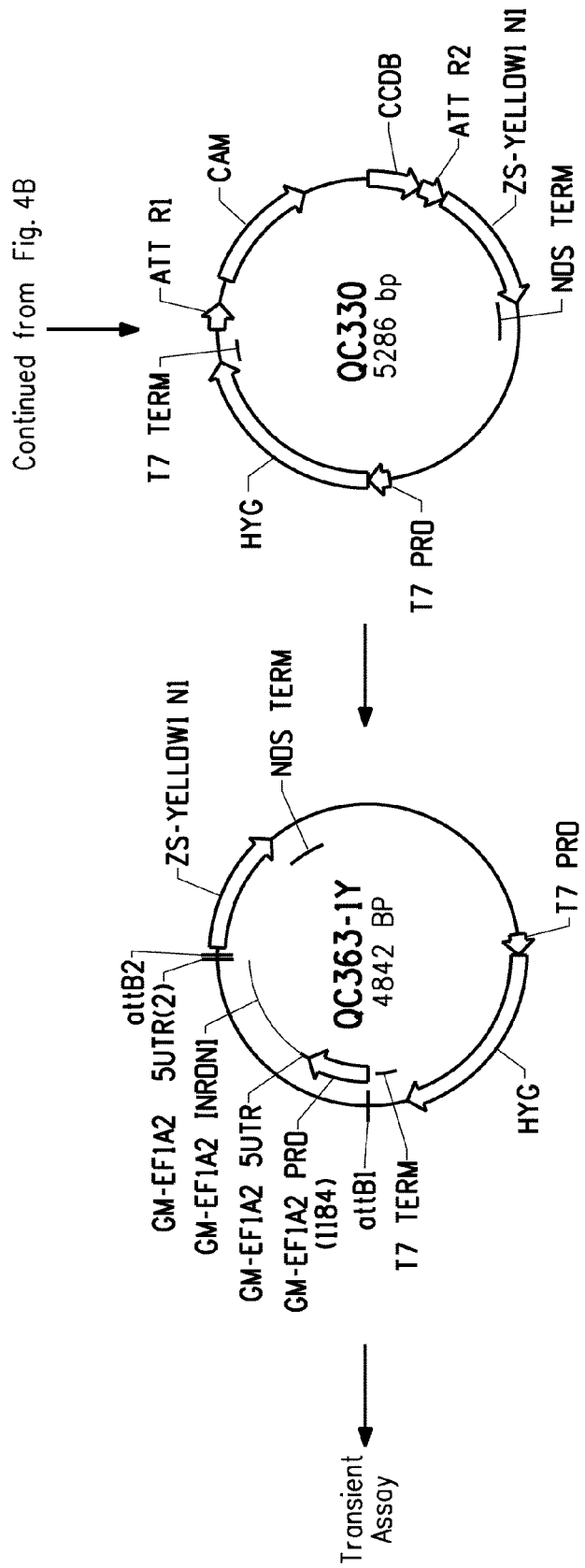
FIG. 4 shows the maps of plasmid pCR8/GW/TOPO, QC363-1, QC300, and QC363-1Y containing the truncated 1184 bp EF1A2 promoter. Promoter deletion constructs QC363-2Y, QC363-3Y, QC363-4Y, and QC363-5Y containing the 924, 682, 477, and 253 bp truncated EF1A2 promoters, respectively, have the same map configuration, except for the truncated promoter sequences.

To define the transcriptional elements controlling the EF1A2 promoter activity, the 1502 bp full length (SEQ ID NO:1) and five 5' unidirectional deletion fragments 1184 bp, 924 bp, 682 bp, 477 bp, and 253 bp in length corresponding to SEQ ID NO:2, 3, 4, 5, and 6, respectively, were made by PCR amplification from the full length soybean EF1A2 promoter contained in the original construct QC363 (FIG. 3). The same antisense primer (SEQ ID NO:9) was used in the amplification by PCR of all the five EF1A2 promoter truncation fragments (SEQ ID NO: 2, 3,4, 5, and 6) by pairing with different sense primers SEQ ID NOs:10, 11, 12, 13, and 14, respectively. Each of the PCR amplified promoter DNA fragments was cloned into the Gateway cloning ready TA cloning vector pCR8/GW/TOPO (Invitrogen) and clones with the correct orientation, relative to the Gateway recombination sites attL1 and attL2, were selected by BamHI+XhoI double restriction enzymes digestion analysis and sequence confirmation (see the example map QC363-1 in FIG. 4). The maps of constructs QC363-2, 3, 4, and 5 containing the EF1A2 promoter fragments SEQ ID NOs:2, 3, 4, 5, and 6 are similar to QC363-1 map and are not shown. The promoter fragment in the right orientation was subsequently cloned into a Gateway destination vector QC330 (SEQ ID NO:49) by Gateway LR clonase reaction (Invitrogen) to place the promoter fragment in front of the reporter gene YFP (see the example map QC363-1Y in FIG. 4). A 21 bp Gateway recombination site attB2 SEQ ID NO:47 was inserted between the promoter and the YFP reporter gene coding region as a result of the Gateway cloning process. The maps of constructs QC363-2Y, 3Y, 4Y, and 5Y containing the EF1A2 promoter fragments SEQ ID NOs: 3, 4, 5, and 6 are similar to QC363-1Y map and not shown. The EF1A2:YFP promoter deletion constructs were delivered into germinating soybean cotyledons by gene gun bombardment for transient gene expression study. The full length EF1A2 promoter in QC363 that does not have the attB2 site located between the promoter and the YFP gene was also included for transient expression analysis. The six EF1A2 promoter fragments analyzed are schematically described in FIG. 5.

Example 7

Transient Expression Analysis of EF1A2:YFP Constructs

The constructs containing the full length and truncated EF1A2 promoter fragments (QC363, QC363-1Y, 2Y, 3Y, 4Y, and 5Y) were tested by transiently expressing the ZS-YEL-LOW1 N1 (YFP) reporter gene in germinating soybean cotyledons. Soybean seeds were rinsed with 10% Tween 20 in sterile water, surface sterilized with 70% ethanol for 2 minutes and then by 6% sodium hypochloride for 15 minutes. After rinsing the seeds were placed on wet filter paper in Petri dish to germinate for 4-6 days under light at 26° C. Green cotyledons were excised and placed inner side up on a 0.7% agar plate containing Murashige and Skoog media for particle gun bombardment. The DNA and gold particle mixtures were prepared similarly as described in EXAMPLE 5 except with more DNA (100 ng/μl). The bombardments were also carried out under similar parameters as described in EXAMPLE 5. YFP expression was checked under a Leica MZFLIII stereo microscope equipped with UV light source and appropriate light filters (Leica Microsystems Inc., Bannockburn, Ill.) and pictures were taken approximately 24 hours after bombardment with 8× magnification and the same camera settings as 1.06 gamma, 0.0% gain, and 2 seconds exposure.

The full length EF1A2 promoter construct QC363, and two deletion constructs QC363-1Y and 2Y had moderate yellow fluorescence signals in transient expression assay by showing the large green/yellow dots (shown as bright white dots in FIG. 6). The attB2 site did not seem to interfere with promoter activity and reporter gene expression. Each dot represented a single cotyledon cell which appeared larger if the fluorescence signal was strong or smaller if the fluorescence signal was weak even under the same magnification. QC363-2Y contains only 211 bp of the promoter upstream of the 5'UTR but showed as strong signals as the full length construct QC363 suggesting that the 211 bp promoter contains all necessary elements for the promoter strength. The three longer deletions constructs QC363-3Y, 4Y, and 5Y in which only a part of the intron and the 5'UTR (2) remained all showed similar and extremely low level expression (FIGS. 5, 6). The expression level difference between QC363-2Y and QC363-3Y suggested that the 5'UTR intron does not have any promoter activity and that the 5'UTR and its upstream as short as 211 bp promoter sequences are sufficient for the effective expression of a reporter gene by the EF1A2 promoter.

Example 8

EF1A:YFP Expression in Stable Transgenic Soybean Plants

YFP gene expression was tested at different stages of transgenic plant development for yellow fluorescence emission under a Leica MZFLIII stereo microscope equipped with a UV light source and appropriate fluorescent light filters. Yellow fluorescence (shown as bright white areas in FIG. 7) was detected early on during somatic embryo development and throughout all stages of transgenic plant development in all tissues tested, such as somatic embryos, leaf, stem, root, flower, pod, and seed. During tissue culture stages of transgenic plant regeneration, fluorescence was uniformly detected in young globular and torpedo stage somatic embryos (FIGS. 7A, B), in cotyledon stages embryos (FIG. 7C), and in mature and dried down embryos (FIG. 7D). Negative control embryos emitted weak red color as did the negative section of a positive embryo cluster (shown as dark grey areas in FIG. 7A) due to auto fluorescence from the chlorophyll contained in soybean green tissues including embryos. Negative controls for other tissue types displayed in FIG. 7 are not shown, but any green tissue such as leaf or stem negative for YFP expression would be red and any white tissue such as root and petal would be dark yellowish under the yellow fluorescent light filter.

When transgenic plantlets were regenerated from somatic embryos, yellow fluorescence was detected in leaf, stem, and root and was retained in all vegetative tissues throughout mature plants. Fluorescence in leaflets collected from plantlets seemed much stronger than that in leaves collected from mature plants probably partly due to weak masking effect of less chlorophyll in young leaves on yellow fluorescence (FIGS. 7E, F). Though trichomes on both sides of a leaf showed fluorescence, it was difficult to determine if the fluorescence signals were specific to the transgenic reporter gene since trichomes fluoresced under different non-specific fluorescent light filters. Fluorescence was readily detected throughout the young stem of plantlets and concentrated in the vascular bundles in the stem of mature plants (FIGS. 7G, N). Fluorescence was detected in all parts of a root (FIG. 7H).

A soybean flower consists of five sepals, five petals including one standard large upper petal, two large side petals, and two small fused lower petals called kneel to enclose ten stamens and one pistil. The pistil consists of a stigma, a style, and an ovary in which there are 2-4 ovules. A stamen consists of a filament, and an anther on its tip. Pollen grains reside inside anther chambers and are released during pollination. Yellow fluorescence was detected in sepals and in the exposed part of petals of a young flower bud when its petals were still mostly enclosed by sepals (FIG. 7I). Fluorescence was detected in all parts including petals, anthers, pollens, filaments, and the stigma, style, and ovary of the pistil when a mature flower was dissected (FIG. 7J-L). Strong yellow fluorescence was also detected in ovules when exposed from the pistil (FIG. 7M).

Strong yellow fluorescence was detected in developing pods and seeds at all stages of the EF1A2:YFP transgenic plants from very young R3 pod of ~5 mm long (FIG. 7O), to full R4 pod of ~20 mm long (FIG. 7P), until mature R5, R6 pod fully filled with seeds (FIGS. 7Q, R). Detail descriptions of soybean development stages can be found in (Fehr and Caviness, CODEN:IWSRBC 80:1-12 (1977)). Since T0 transgenic plants are hemizygous in nature, the embryos of their progeny T1 seeds will segregate according to Mendel's law, but the seed coats will not segregate since they are developed from the maternal tissue ovule coats. A negative T1 seed would only have its coat fluorescing but not its embryo (FIG. 7R). In conclusion, EF1A2:YFP expression was detected with high levels in all tissues throughout transgenic plant development indicating that the soybean EF1A2 promoter is a strong constitutive promoter.

What is claimed is:

1. A recombinant DNA comprising a nucleotide sequence comprising the sequence set forth in SEQ ID NO:1, SEQ ID NO:2, SEQ ID NO:3, SEQ ID NO:4, SEQ ID NO:5, or SEQ ID NO:6, operably linked to at least one heterologous sequence, wherein said nucleotide sequence has constitutive promoter activity.

2. A recombinant DNA construct comprising a nucleotide sequence comprising bases 800-1502 of SEQ ID NO:1, bases 482-1184 of SEQ ID NO:2, or 212-924 SEQ ID NO:3 and at least 211 contiguous nucleotides upstream of SEQ ID NO:1, SEQ ID NO:2, or SEQ ID NO:3, operably linked to at least one heterologous sequence, wherein said nucleotide sequence has constitutive promoter activity.

3. A vector comprising the recombinant DNA construct of any one of claim 1 or 2.

4. A cell comprising the recombinant DNA construct of any one of claim 1 or 2.

5. The cell of claim 4, wherein the cell is a plant cell.

6. A transgenic plant having stably incorporated into its genome the recombinant DNA construct of any one of claim 1 or 2.

7. The transgenic plant of claim 6 wherein said plant is selected from the group consisting of dicotyledonous plants.

8. The plant of claim 7 wherein the plant is soybean.

9. A transgenic seed produced by the transgenic plant of claim 7, wherein the transgenic seed comprises the recombinant DNA construct.

10. A method of expressing a coding sequence or a functional RNA in a plant comprising:
   a) introducing the recombinant DNA construct of any one of claim 1 or 3 into the plant, wherein the at least one heterologous sequence comprises a coding sequence or encodes a functional RNA;
   b) growing the plant of step a); and
   c) selecting a plant displaying expression of the coding sequence or the functional RNA of the recombinant DNA construct.

11. A method of transgenically altering a marketable plant trait, comprising:
   a) introducing a recombinant DNA construct of any one of claim 1 or 3 into the plant;
   b) growing a fertile, mature plant resulting from step a); and
   c) selecting a plant expressing the at least one heterologous nucleotide sequence in at least one plant tissue based on the altered marketable trait.

12. The method of claim 11 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

13. A method for altering expression of at least one heterologous nucleic acid fragment in plant comprising:
   (a) transforming a plant cell with the recombinant expression construct of any one of claim 1 or 2;
   (b) growing fertile mature plants from transformed plant cell of step (a); and
   (c) selecting plants containing the transformed plant cell wherein the expression of the heterologous nucleic acid fragment is increased or decreased.

14. The method of claim 13 wherein the plant is a soybean plant.

15. A method for expressing a yellow fluorescent protein ZS-YELLOW1 N1 in a plant cell comprising:
   (a) transforming a plant cell with a recombinant expression construct comprising at least one ZS-YELLOW1 N1 (YFP) nucleic acid fragment operably linked to a promoter wherein said promoter consists essentially of the nucleotide sequence set forth in SEQ ID NOs:1, 3, or 4; and,
   (b) growing the transformed plant cell under conditions for expression of the recombinant DNA construct, wherein expression of the recombinant DNA construct results in production of increased levels of ZS-YELLOW1 N1 protein in the transformed host cell when compared to a corresponding nontransformed plant cell.

16. A plant stably transformed with a recombinant expression construct comprising a soybean promoter and a heterologous nucleic acid fragment operably linked to said promoter, wherein said promoter is a capable of controlling expression of said heterologous nucleic acid fragment in a plant cell, and further wherein said promoter comprises at least 211 contiguous nucleotides upstream of the 5' untranslated region of SEQ ID NO:1.

17. The recombinant DNA construct according to claim 1, wherein the heterologous nucleic acid sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat and salt resistance in plants.

18. The recombinant DNA construct according to claim 1, wherein the heterologous nucleic acid sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

* * * * *

UNITED STATES PATENT AND TRADEMARK OFFICE
CERTIFICATE OF CORRECTION

| | | |
|---|---|---|
| PATENT NO. | : 8,697,857 B2 | Page 1 of 1 |
| APPLICATION NO. | : 12/274443 | |
| DATED | : April 15, 2014 | |
| INVENTOR(S) | : Zhongsen Li | |

It is certified that error appears in the above-identified patent and that said Letters Patent is hereby corrected as shown below:

In the Claims:

Column 77, line 42, Claim 1 should read A recombinant DNA --construct--

Signed and Sealed this
First Day of July, 2014

Michelle K. Lee
*Deputy Director of the United States Patent and Trademark Office*